US009675016B2

(12) United States Patent
Shetty et al.

(10) Patent No.: US 9,675,016 B2
(45) Date of Patent: Jun. 13, 2017

(54) DOWNY MILDEW RESISTANT CUCUMBER PLANTS

(71) Applicant: SEMINIS VEGETABLE SEEDS, INC., St. Louis, MO (US)

(72) Inventors: Nischit Shetty, Ft. Myers, FL (US); Henk van Kooten, Veenendaal (NL); Bruno Sipeyre, Garons (FR); Albert Grit, Ekmelo (NL); Joseph J. King, Davis, CA (US); Marie Gretenkort, Grimsby (GB); M. Yolanda Duran, Aguadulce (ES)

(73) Assignee: Seminis Vegetable Seeds, Inc., Woodland, CA (US)

( * ) Notice: Subject to any disclaimer, the term of this patent is extended or adjusted under 35 U.S.C. 154(b) by 54 days.

(21) Appl. No.: 14/321,542

(22) Filed: Jul. 1, 2014

(65) Prior Publication Data

US 2015/0026838 A1    Jan. 22, 2015

Related U.S. Application Data

(62) Division of application No. 12/424,452, filed on Apr. 15, 2009, now Pat. No. 8,859,859.

(60) Provisional application No. 61/045,551, filed on Apr. 16, 2008.

(51) Int. Cl.

| | |
|---|---|
| *A01H 5/08* | (2006.01) |
| *A01H 5/10* | (2006.01) |
| *A01H 1/04* | (2006.01) |
| *A01G 1/00* | (2006.01) |
| *A01H 1/02* | (2006.01) |
| *C12Q 1/68* | (2006.01) |

(52) U.S. Cl.
CPC .............. *A01H 5/08* (2013.01); *A01G 1/001* (2013.01); *A01H 1/02* (2013.01); *A01H 1/04* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,237,019 | B2 | 8/2012 | Van den Ackerveken et al. |
| 2009/0170703 | A1 | 7/2009 | Van den Ackerveken et al. |
| 2011/0126309 | A1 | 5/2011 | Caldwell et al. |
| 2015/0059016 | A1 | 2/2015 | Caldwell et al. |

FOREIGN PATENT DOCUMENTS

| | | |
|---|---|---|
| JP | 2004-313062 | 11/2004 |
| KR | 10-1988-0012145 | 11/1988 |
| WO | WO 2007/053015 A2 | 5/2007 |
| WO | WO 2009/129314 | 10/2009 |

OTHER PUBLICATIONS

Wehner et al 1997 Crop Science 37:1331-1340 (provided in IDS).*
Block et al 2005 HortScience 40:416-420 (provided in IDS).*
U.S. Appl. No. 14/285,509, filed May 22, 2014, Caldwell et al.
U.S. Appl. No. 12/092,253, Van den Ackerveken et al.
U.S. Appl. No. 12/910,478, Caldwell et al.
Angelov et al., "Selecting downy mildew-resistant short-fruited cucumbers," In: *Proc. Cucurbitaceae*: Proceedings of the 7th Eucarpia meeting on cucurbit breeding and genetics, p. 135, Kazir (Ed.), Ma'ale Ha Hamisha, Israel, Mar. 19-23, 2000.
Angelov et al., "Two races of *Pseudoperonospora cubensis* on cucumbers in Bulgaria," In: *Proc. Cucurbitaceae*; Proceedings of the 7th Eucarpia meeting on cucurbit breeding and genetics, pp. 81-83, Kazir (Ed.), Ma'ale Ha Hamisha, Israel, Mar. 19-23, 2000.
Block et al., "Powdery Mildew Resistance in the U.S. National Plant Germplasm System Cucumber Collection", *HortScience* 40(2):416-420, 2005.
Bradeen et al., "Towards an Expanded and integrated linkage map of cucumber (*Cucumis sativus* L.)," *Genome, NRC Canada*, 44(1):111-119, 2001.
Bakr et al., "Genetics of resistance to downy mildew in cucumbers," *HortScience*, 28(5):506, 1993.
Call et al., "Screening Cucumber for Resistance to Downy Mildew Caused by *Pseudoperonospora cubensis*," Crop Sci. (52); 577-592; Mar.-Apr. 2012.
Call, "Studies on resistance to downy mildew in Cucumber (*Cucumis sativus* L.) caused by *Pseudoperonospora cubensis*," Thesis, North Carolina State University, 2010.
Cohen, "A laboratory technique for identifying resistance to cucumber downy mildew," *Phytoparasitica*, 4(3):209, 1976.
Cohen, "Quantitation of resistance of cucumbers and cantaloups to *Pseudoperonospora cubensis,*" *Phytoparasitica*, 4(1):25-31, 1976.
Criswell et al., "Screening cucumber for resistance to the new downy mildew," PPI 2007 Annual Meeting and Pickle Fair, Memphis, TN, Oct. 4, 2007.
Criswell, "Screening cucumber (*Cucumis sativus*) for resistance to downy mildew (*Pseudoperonospora cubensis*)," North Carolina State University, Master's Thesis, dated Jul. 22, 2008.
Database EMBL, XP002693073, 2004.
Ding et al., "A Novel RAPD and SCAR Marker of the Resistant Gene for Downy Mildew (*dm*) in Cucumber," *Acta Bot. Boreal.-Occident. Sin.*, 27(9):1747-1751, 2007.
Dhillon et al., "Evaluation of landraces of cucumber (*Cucumis sativus* L.) for resistance to downy mildew (*Pseudoperonospora cubensis*)," *Plant Genetics Resources Newsletter*, 119:59-61, 1999.
Doruchowski et al., "F1 hybrid pickling cucumbers developed for increased yield, earliness and resistance to downy mildew (*Pseudoperonospora cubensis*)," *Acta Hort.*, 510:45-46, 2000.
Doruchowski et al., "Tolerance of polish new cucumber F1 hybrids to downy mildew (*Pseudoperonospora cubensis* Berk & Curt) and limitation or elimination chemical disease control," *Acta Hort.*, 371:129-133, 1994.

(Continued)

*Primary Examiner* — Brent Page
(74) *Attorney, Agent, or Firm* — Dentons US LLP; Matthew Madsen, Esq.

(57) ABSTRACT

The present invention relates to cucumber lines having increased resistance to Downy Mildew. The present invention also relates to parts of cucumber plants from lines having increased Downy Mildew resistance, including seeds capable of growing cucumber plants with increased Downy Mildew resistance. Further provided are methods of producing such plants by genetic marker assisted selection.

18 Claims, 2 Drawing Sheets

(56) References Cited

OTHER PUBLICATIONS

Fan et al., Population development by phenotypic selection with subsequent marker-assisted selection for line extraction in cucumber (*Cucumis sativus* L.), *Theor. Appl. Genet.*, 112:843-855, 2006.
Horejsi et al., Linkage of random amplified polymorphic DNA markers to downy mildew resistance in cucumber (*Cucumis sativus* L.),*Euphytica*, 115:105-113, 2000.
Horejsi et al., "Tagging a downy mildew resistance gene in cucumber using RAPD markers," *HortSci.*, 31(4):624, 1996.
Horejsi, "Random amplified polymorphic DNA and sequence characterized amplified regions for studies of genetic diversity and downy mildew resistance in cucumber," Dissertation, Ph.D.—Plant Breeding and Plant Genetics, University of Wisconsin, 1998.
Huang et al., "The genome of the cucumber, *Cucumis sativus* L.," *Nature Genetics*, 41(12):1275-1281, 2009.
Jurjevic et al., "Tolerance of pickling cucumber cultivars to downy mildew infection *Pseudoperonospora cubensis* (Berk. Et Curt.) rostow and its effect on yield," *Fragmenta Phytomedica et Herbologica*, 24(2):15-27, 1996. (Certified translation).
Lebeda et al., "Peroxidase isozyme polymorphism as a potential marker for detection of field resistance in *Cucumis sativus* to cucumber downy mildew (*Pseudoperonospora cubensis* (Berk. Et Curt.) Rostov.)," J. of Plant Diseases & Protect., 102(5):467-471, 1995.
Lebeda, "Cucurbit downy mildew (*Pseudoperonospora cubensis*)— biology, ecology, epidemiology, host-pathogen interaction and control," *Eur. J. Plant Pathol.*, DOI 10.1007/s10658-010-9658-1, Jul. 25, 2010.
Lebeda, "Screening of wild cucumis species against downy mildew (*Pseudoperonospora cubensis*) isolates from cucumbers," *Phytoparasitica*, 20(3):203-210, 1992.
Lebeda, "Susceptibility of accessions of cucumis sativus to *Pseudoperonospora cubensis*," *Tests of Agrochemicals and Cultivars*, 13:102-103, 1992.
Lisitsin et al., "Evaluation of specimen cucumber cultivars for breeding against bacteriosis and downy mildew," *Ukrainian Research Institute of Vegetable Crops and Melon Production*, 35:82-84, 1990. (Certified translation).
Luo Guifen et al., "Relationship of sugar and lignin content in cucumber leaves to induced resistance to downy mildew," *Acta Phytopathologica Sinica*, 27(1):65-69, 1997. (Certified Translation).
McFerson et al., "Cucumber resistance to downy mildew in the laboratory greenhouse and field," *HortSci.*, 13(3)(Supp.):344, 1978.
Medvedeva et al., "Agrobiological evaluation of specimen cucumber cultivars promising for breeding against downy mildew," *Trudy Po Prikladnoi Botanike, Genetike I Selektsii*, 77:25-28, 1983. (Certified Translation).
Meglic et al., "Genetic diversity in cucumber (*Cucumis sativus* L.): II. An evaluation of selected cultivars released between 1846 and 1978," *Genetic Resources and Crop Evolution*, 43(6):547-558,1996.
Monsanto ad for Seminis Vegetable Seeds; "Introducing Seminis® Downy Mildew Resistant Cucumbers," us.seminis.com; 2012.
Neykov et al., "Introduced cucumber cultivars relatively resistant to pseudoperonospora cubensis in Bulgaria," *Acta Hort.*, 220:115-119, 1987.
Pierce et al., "Review of genes and linkage groups in cucumber," *Hort. Sci.*, 25(6):605-615, 1990.
Pados et al., "Further results in the cultivation of peronospora-resistant cucumber species," *Novenyvedelem*, 24(7):311. (Certified Translation).
Pershin et al., "Quantitative approach to genetical study of plant resistance to diseases. IV. Interaction of genetic systems of cucumber resistance to powdery and downy mildew," *Genetika*, 24(3):484-493, 1988. (Certified Translation).
Pershin et al., "Quantitative approach to the study of genetics of disease resistance in plants—IV. Interaction of genetic systems of powdery mildew and downy mildew resistance in cucumber," *Soviet Genetics*, 24(3):333-340, 1988.
Petrov et al., "Resistance to downy mildew, *Pseudoperonospora cubensis*, in cucumbers," *Acta Hort.*, 510:203-209, 2000.
Pivovarov, "Cucumber breeding for resistance to false mildew (*Pseudoperonospora cubensis* R.) using various ecological-geographic zones," In: Eucarpia: Proc. of the 3rd Meeting on Breeding of Cucumbers and Melons, p. 40-46, Jul. 2-5, 1984, Plovdiv, Bulgaria.
Reddy et al., "Evaluation of cucumber genotypes for their performance and resistance to downy mildew disease," *Ad. Agric. Res. India*, 7:175-1771997.
Ren et al., "An integrated genetic and cytogenetic map of the cucumber genome," *PLOS One*, 4(6)(e5795):1-8, Jun. 4, 2009.
Sakata et al., "QTL analysis of powdery mildew resistance in cucumber (*Cucumis sativus* L.)," *Theor Appl Genet*, 112:243-250, 2006.
Savory et al., "The cucurbit downy mildew pathogen *Pseudoperonospora cubensis*," *Mol. Plant Pathol.*, DOI: 10.1111/J. 1364-3703.2010.00670.X, 2010.
Shetty et al., "Evidence for downy mildew races in cucumber tested in Asia, Europe, and North America," *Scientia Horticulturae*, 94:231-239, 2002.
Smiech et al., "Attempt to select cucumber (*Cucumis sativus*) double haploid lines to downy mildew tolerance by molecular markers," *Curcurbitaceae 2008: Proceedings of the IXth EUCARPIA meeting on genetics and breeding of Cucurbitaceae*, pp. 441-444, 2008.
St. Amand et al., Crop loss to 14 diseases in cucumber in North Carolina for 1983 to 1988, *Cucurbit Genetics Coop.*, 14:15-17, 1991.
Staub et al., "Evaluation of cucumber germplasm for six pathogens," In: Proceedings Cucurbitaceae 89: evaluation and enhancement of cucurbit germplasm, pp. 149-153, Thomas (Ed.), Charleston, SC, Nov. 29-Dec. 2, 1989.
Staub et al., "Selection for multiple disease resistance reduces cucumber yield potential," *Euphytica*, 67:205-213, 1993.
Tarakanov et al., "Methodology for breeding cucumbers for resistance to downy mildew," In: Selektsiya, Semenovodstvo I Sortovaya Tekhnologiya Proizvodstva Ovoshchei, pp. 13-17, 1998. (Certified Translation).
Van Vliet et al., "Inheritance of resistance to pseudoperonospora cubensis Rost. In cucumber (*Cucumis sativus* L.)," *Euphytica*, 23:251-255, 1974.
Van Vliet et al., "Relation in the inheritance of resistance to pseudoperonospora cubensis Rost and sphaerotheca fuliginea poll. in cucumber (*Cucumis sativus* L.), " *Euphytica*, 26:793-796, 1977.
Wan et al., "Identification and characterization of potential NBS-encoding resistance genes and induction kinetics of a putative candidate gene associated with downy mildew resistance in *Cucumis*," *BMC Pl. Biol.*, 10(1):186, 2010.
Weber et al., "The resistance of cucumbers to cucumber mosaic virus, powdery mildew (*Spaerotheca fuliginea* [schlecht et fr.] pollaci) and downy mildew (*Pseudoperonospora cubensis* . . . ," *Arch Phytopathol Pflanzenschutz*, 27(5):361-367, 1991. (Certified Translation).
Wehner et al., "Downy mildew resistance of the cucumber germplasm collection in North Carolina field tests," *Crop Sci.*, 37:1331-1340, 1997.
Woltman et al., Evaluation of cucumber (*Cucumis sativus*) cultivars grown in eastern Europe and progress in breeding for resistance to angular leaf spot (*Pseudomonas syringae* pv. Lachrymans), *Eur. J. Plant Path.*, 122:385-393, 2008.
Yeboah et al., "A genetic linkage map of cucumber (*Cucumis sativus* L) combining SRAP and ISSR markers," *African Journal of Biotechnology*, 6(24):2784-2791, Dec. 17, 2007.
Zhou et al., "Molecular analysis of introgression lines from *Cucumis hystrix* Chakr. to *C. sativus* L," *Scienta Horticulturae*, 119(3):232-235, 2009.
Notification of the Transmittal of the International Search Report and the Written Opinion of the International Searching Authority, or the Declaration for PCT/US2010/53812, dated Mar. 30, 2011.

(56) References Cited

OTHER PUBLICATIONS

USPTO; Non-final Office Action for U.S. Appl. No. 12/910,478 dated Feb. 15, 2013.
Response to Non-final Office Action for U.S. Appl. No. 12/910,478 dated Jun. 11, 2013.
USPTO; Final Office Action for U.S. Appl. No. 12/910,478 dated Oct. 8, 2013.
Response to Office Action regarding U.S. Appl. No. 12/910,478, dated Nov. 26, 2013.
USPTO; Notice of Allowance regarding U.S. Appl. No. 12/910,478, dated Mar. 6, 2014.
USDA, ARS, National Genetic Resources Program. Germplasm Resources Information Network—(GRIN). [Online Database] National Germplasm Resources Laboratory, Beltsville, Maryland. Available: http://www.ars-grin.gov/cgi-bin/npgs/acc/display.pl?1167933, retrieved on Jun. 12, 2011.
USDA, ARS, National Genetic Resources Program. Germplasm Resources Information Network—(GRIN). [Online Database] National Germplasm Resources Laboratory, Beltsville, Maryland. Available: http://www.ars-grin.gov/cgi-bin/npgs/html/cno_acc.pl?56705, retrieved on Sep. 14, 2011.
Fazio et al., "Development and Characterization of PCR Markers in Cucumber," *J. Amer. Soc. Hort. Sci.* 127(4):545-557, 2002.
Fazio et al., "Comparative analysis of response to phenotypic and marker-assisted selection for multiple lateral branching in cucumber (*Cucumis sativus* L.)," *Theor. Appl. Genet.* 107:875-883, 2003.
Xu et al., "Marker-Assisted Selection in Plant Breeding: From Publications to Practice," *Crop Sci.* 48:391-407, 2008.
Korean Office Action regarding Korean Application No. 10-2010-7025553, dated Mar. 31, 2016.
Korean Office Action regarding Korean Application No. 10-2010-7025553, dated Mar. 31, 2016. (English translation).
USPTO: Non-final Office Action regarding U.S. Appl. No. 14/285,509, dated Dec. 15, 2016.

* cited by examiner

```
                             SEQUENCE LISTING

<160> NUMBER OF SEQ ID NOS: 17

<210> SEQ ID NO 1
   <211> LENGTH: 29
   <212> TYPE: DNA
   <213> ORGANISM: Artificial
   <220> FEATURE:
   <223> OTHER INFORMATION: Synthetic Primer

<400> SEQUENCE: 1
gaatagatag gctacacttt tccctcttg                                          29

<210> SEQ ID NO 2
   <211> LENGTH: 31
   <212> TYPE: DNA
   <213> ORGANISM: artificial
   <220> FEATURE:
   <223> OTHER INFORMATION: Synthetic Primer

<400> SEQUENCE: 2
gtataaaact tgagtgaatt taatgcatga a                                       31

<210> SEQ ID NO 3
   <211> LENGTH: 35
   <212> TYPE: DNA
   <213> ORGANISM: Artificial
   <220> FEATURE:
   <223> OTHER INFORMATION: Synthetic Primer

<400> SEQUENCE: 3
tgtttcataa ctacagcttc atgttaaata ttact                                   35

<210> SEQ ID NO 4
   <211> LENGTH: 25
   <212> TYPE: DNA
   <213> ORGANISM: Artificial
   <220> FEATURE:
   <223> OTHER INFORMATION: Synthetic Primer

<400> SEQUENCE: 4
tagtttcttt cttgctggac gaacc                                              25

<210> SEQ ID NO 5
   <211> LENGTH: 21
   <212> TYPE: DNA
   <213> ORGANISM: Artificial
   <220> FEATURE:
   <223> OTHER INFORMATION: Synthetic Primer

<400> SEQUENCE: 5
tatgggctat gtgaaactct t                                                  21

<210> SEQ ID NO 6
   <211> LENGTH: 21
   <212> TYPE: DNA
   <213> ORGANISM: Artificial
   <220> FEATURE:
   <223> OTHER INFORMATION: Synthetic Primer

<400> SEQUENCE: 6
```

-continued

```
agcgtgacaa ctacaaaaca t                                              21

<210> SEQ ID NO 7
<211> LENGTH: 23
<212> TYPE: DNA
<213> ORGANISM: Artificial
<220> FEATURE:
<223> OTHER INFORMATION: Synthetic Primer

<400> SEQUENCE: 7
gaaataaatg gatgaagcga gga                                            23

<210> SEQ ID NO 8
<211> LENGTH: 27
<212> TYPE: DNA
<213> ORGANISM: Artificial
<220> FEATURE:
<223> OTHER INFORMATION: Synthetic Primer

<400> SEQUENCE: 8
gttcgttgat cagtgtgata tttcaat                                        27

<210> SEQ ID NO 9
<211> LENGTH: 21
<212> TYPE: DNA
<213> ORGANISM: Artificial
<220> FEATURE:
<223> OTHER INFORMATION: Synthetic Primer

<400> SEQUENCE: 9
atcggtcttt gccacctttt g                                              21

<210> SEQ ID NO 10
<211> LENGTH: 28
<212> TYPE: DNA
<213> ORGANISM: Artificial
<220> FEATURE:
<223> OTHER INFORMATION: Synthetic Primer

<400> SEQUENCE: 10
aggagggaca gagagaattt gatataat                                       28

<210> SEQ ID NO 11
<211> LENGTH: 27
<212> TYPE: DNA
<213> ORGANISM: Artificial
<220> FEATURE:
<223> OTHER INFORMATION: Synthetic Primer

<400> SEQUENCE: 11
tccgttttag gtgattgtca aatacat                                        27

<210> SEQ ID NO 12
<211> LENGTH: 21
<212> TYPE: DNA
<213> ORGANISM: Artificial
<220> FEATURE:
<223> OTHER INFORMATION: Synthetic Primer

<400> SEQUENCE: 12
tgtttggaag ggtttcttgg g                                              21

<210> SEQ ID NO 13
<211> LENGTH: 18
<212> TYPE: DNA
<213> ORGANISM: Artificial
```

```
<220> FEATURE:
<223> OTHER INFORMATION: Synthetic Primer

<400> SEQUENCE: 13
tgccatgtcg ccaacagt                                                    18

<210> SEQ ID NO 14
<211> LENGTH: 23
<212> TYPE: DNA
<213> ORGANISM: Artificial
<220> FEATURE:
<223> OTHER INFORMATION: Synthetic Primer

<400> SEQUENCE: 14
tcaagccata gtctaaccca tgc                                              23

<210> SEQ ID NO 15
<211> LENGTH: 25
<212> TYPE: DNA
<213> ORGANISM: Artificial
<220> FEATURE:
<223> OTHER INFORMATION: Synthetic Primer

<400> SEQUENCE: 15
cgctatatca tggatggcta gaaat                                            25

<210> SEQ ID NO 16
<211> LENGTH: 30
<212> TYPE: DNA
<213> ORGANISM: Artificial
<220> FEATURE:
<223> OTHER INFORMATION: Synthetic Primer

<400> SEQUENCE: 16
aaagttgata gtgcatgagt tggtaaaata                                       30

<210> SEQ ID NO 17
<211> LENGTH: 22
<212> TYPE: DNA
<213> ORGANISM: Artificial
<220> FEATURE:
<223> OTHER INFORMATION: Synthetic Primer

<400> SEQUENCE: 17
tccgcttatg ggtttttgtg ag                                               22
```

DOWNY MILDEW RESISTANT CUCUMBER PLANTS

CROSS REFERENCE TO RELATED APPLICATIONS

This application is a divisional of U.S. application Ser. No. 12/424,452, filed Apr. 15, 2009, which claims priority to U.S. Provisional Patent Application Ser. No. 61/045,551, filed Apr. 16, 2008, the entire disclosures of which are incorporated herein by reference.

FIELD OF THE INVENTION

The invention relates to cucumber plants having Downy Mildew resistance and methods for producing such plants.

BACKGROUND OF THE INVENTION

Cucumber (*Cucumis sativus* L.) is a popular vegetable crop that has been cultivated for several thousand years and is grown worldwide. Cucumber plants are grown in a wide range of climates, and in open fields as well as greenhouses. The two main types of cucumber fruit grown commercially today are fresh market (slicing) and processing (pickling).

Downy Mildew (DM) is caused by the fungus *Pseudoperonospora cubensis* (P.c.), which causes significant crop losses among many Cucurbit species, including cucumber. The disease is found worldwide and favors moist, temperate conditions. The disease affects greenhouse grown plants, and plants grown in the field. DM is one of the most important foliar diseases of cucurbits, and can reduce fruit yield and quality, and may kill susceptible seedlings.

Symptoms of DM infection are variable. Initial symptoms include sharp, irregular yellow lesions on the upper surface of the leaves, which eventually become more distinct on both sides of the leaves. The underside of the leaves may exhibit a whitish-gray, brown, or light blue growth, particularly under moist conditions. This downy growth is spores produced on the lower surface of the lesion. A general yellowing of affected leaves typically occurs as the lesions coalesce into one large lesion, eventually causing the leaf to wilt and die. The disease can progress quite rapidly, killing foliage in a matter of a few days and resulting in poor fruit production and quality. Cucumber fruit are not affected directly, but major defoliation exposes the fruit to sunscald. Once it appears on a crop, DM rapidly spreads by wind, or splashing rain and/or irrigation water. Disease management and prevention requires destruction of all plants from infected nurseries and disinfection of the facilities. Emergence of a new isolate of DM has also overcome some previously known resistant lines. Thus, there is a need for new cucumber varieties having resistance to DM.

SUMMARY OF THE INVENTION

In one aspect, the invention provides a method of producing a cucumber plant having resistance to Downy Mildew comprising the steps of (a) crossing a cucumber plant of accession PI197088 with a second cucumber plant having at least one desired trait; and (b) selecting at least a first progeny cucumber plant resulting from the crossing that comprises resistance to Downy Mildew and the desired trait. In one embodiment, a method is provided wherein the desired trait is selected from the group consisting of: fruit size, shape, color, surface appearance; seed number, seed size, locule number; pericarp thickness and toughness; taste, bitterness, the presence of tubercles, shelf life, plant vigor, leaf shape, leaf length, leaf color, plant height, whether the plant is determinate or not, time to maturity, adaptation to field growth, adaptation to greenhouse growth, fruit quality acceptable to market, and resistance to one or more diseases or disease causing organisms selected from the group consisting of *Verticillium* wilt, root knot nematodes, Tobacco Mosaic Virus, Cucumber scab, Powdery mildew, Target spot, Cucumber Mosaic Virus, *Fusarium* wilt, *Papaya* Ringspot Virus, and Zucchini Yellow Mosaic Virus.

In specific embodiments, selecting the first progeny comprises identifying the presence of at least a first genetic marker in the first progeny that is genetically linked to a locus contributing to Downy Mildew resistance. In another embodiment, selecting the first progeny further comprises selecting the progeny based on the presence of a plurality of genetic markers from the second cucumber plant present in the progeny. In yet other embodiments, the genetic marker is selected from the group consisting of markers CAPs_21826, CAPs_ENK60, CAPs_ENK59, CAPs_17170, CAPs_17179, CAPs_18229, CAPs_17563/66, and CAPs_ENK70. In certain embodiments, the genetic marker is selected from the group consisting of CAPs_ENK60, CAPs_17170, and CAPs_17563/66.

In a further embodiment, the method further comprises the step of: (c) crossing the progeny plant with itself or a third plant to produce a progeny plant of a subsequent generation. In another embodiment, the method further comprises the steps of: (d) crossing the progeny plant of a subsequent generation with itself or a second plant; and (e) repeating steps (c) and (d) for an additional 3-10 generations to produce an inbred cucumber plant derived from the cucumber accession PI197088. In one embodiment, the method may be defined as one wherein said progeny plant of a subsequent generation is selected for crossing based on the presence of resistance to Downy Mildew and the desired trait. In certain embodiments the progeny plant of a subsequent generation is selected at each generation for crossing based on the presence of the resistance to Downy Mildew and desired trait. In other embodiments, the method may be defined as one wherein selecting the progeny plant of a subsequent generation comprises identifying the presence of at least a first genetic marker in the first progeny that is genetically linked to a locus contributing to Downy Mildew resistance. In particular embodiments, selecting the progeny plant of a subsequent generation further comprises selecting the progeny based on the presence of a plurality of genetic markers from the second cucumber plant present in the progeny. In other embodiments, step (e) is repeated a sufficient number of generations to obtain an inbred cucumber plant that comprises the resistance to Downy Mildew and otherwise comprises the agronomic traits of the second cucumber plant.

In another aspect, the invention provides a plant produced by the method wherein step (e) is repeated a sufficient number of generations to obtain an inbred cucumber plant that comprises the resistance to Downy Mildew and otherwise comprises the agronomic traits of the second cucumber plant In yet another aspect, a seed is provided of a cucumber line selected from the group consisting of ASL147-2027, EUR154-1012GY, EUR154-1021GY, GSP33-1094GY, GPN33-1093GY, representative samples of seed of said lines having been deposited under ATCC Accession Number PTA-9375, ATCC Accession Number PTA-8930, ATCC Accession Number PTA-8931, ATCC Accession Number PTA-8953, and ATCC Accession Number PTA-8954, respectively.

In still yet another aspect, the invention provides a plant grown from seed of a cucumber line selected from the group consisting of ASL147-2027, EUR154-1012GY, EUR154-1021GY, GSP33-1094GY, GPN33-1093GY, 03/8020-20_TUP03_DMFL_1 03/8024-19_TUP03_DMFL_1, and 03/8039-5_TUP03_DMFL_1. The invention also provides a plant part of such a plant. In certain embodiments the plant part is selected from the group consisting of a leaf, fruit, pollen, an ovule and a cell.

In still yet another aspect, the invention provides a cucumber plant, or a part thereof, having all the physiological and morphological characteristics of the cucumber plant selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1.

Another aspect of the invention provides a tissue culture of regenerable cells of a cucumber line selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1. In certain embodiments, the tissue culture comprises cells or protoplasts from a plant part selected from the group consisting of embryos, meristems, cotyledons, pollen, leaves, anthers, roots, root tips, pistil, flower, seed and stalks. The invention also provides a cucumber plant regenerated from the tissue, wherein the regenerated plant expresses all of the physiological and morphological characteristics of a plant selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1.

In another aspect, the invention provides a method of producing cucumber seed, comprising crossing the plant selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, with itself or a second cucumber plant. In one embodiment, the seed is an F1 hybrid seed. In another aspect, the invention provides an F1 hybrid plant produced by growing the seed.

In yet another aspect, the invention provides a method for producing a seed of a line ASL147-2027, EUR154-1012GY, EUR154-1021GY, GSP33-1094GY, GPN33-1093GY, 03/8020-20_TUP03_DMFL_1, 03/8024-19_TUP03_DMFL_1, or 03/8039-5_TUP03_DMFL_1 cucumber plant comprising the steps of: (a) crossing a cucumber plant of a line selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, with a second cucumber plant; and (b) allowing seed of a line ASL147-2027, EUR154-1012GY, EUR154-1021GY, GSP33-1094GY, GPN33-1093GY, 03/8020-20_TUP03_DMFL_1, 03/8024-19_TUP03_DMFL_1, or 03/8039-5_TUP03_DMFL_1-derived cucumber plant to form.

In a further aspect, the invention provides a method of vegetatively propagating a line ASL147-2027, EUR154-1012GY, EUR154-1021GY, GSP33-1094GY, GPN33-1093GY, 03/8020-20_TUP03_DMFL_1, 03/8024-19_TUP03_DMFL_1, or 03/8039-5_TUP03_DMFL_1 cucumber plant, comprising the steps of: (a) collecting tissue capable of being propagated from a plant of claim 16; (b) cultivating said tissue to obtain proliferated shoots; and (c) rooting said proliferated shoots to obtain rooted plantlets. In a certain embodiment, the method further comprises growing plants from said rooted plantlets.

In yet another embodiment is provided a method of introducing a desired trait into a cucumber line selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, comprising: (a) crossing a plant of a line selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, with a second cucumber plant that comprises a desired trait to produce F1 progeny; (b) selecting an F1 progeny that comprises the desired trait; (c) crossing the selected F1 progeny with a plant of a line selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, to produce backcross progeny; (d) selecting backcross progeny comprising the desired trait and the physiological and morphological characteristic of a cucumber line selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1; and (e) repeating steps (c) and (d) three or more times in succession to produce selected fourth or higher backcross progeny that comprise the desired trait. Another embodiment of the invention is a cucumber plant produced by such a method.

Another aspect of the invention relates to a method of producing a plant of a cucumber line selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, comprising an added desired trait, the method comprising introducing a transgene conferring the desired trait into a plant of cucumber a line selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1.

Yet another aspect of the invention provides a plant of a cucumber line that exhibits one or more traits selected from the group consisting of: resistance to Angular leaf spot, Anthracnose race 1, Cucumber Scab, Downy mildew, Powdery Mildew, *Papaya* Ringspot, Zucchini Yellow Mosaic, Cucumber Mosaic Virus, and fruit quality acceptable to market, wherein the combination of traits is controlled by genetic means for the expression of such one or more traits found in a cucumber line selected from the group consisting of: ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1. A seed of a plant produced by such a method is another embodiment of the invention.

The invention also provides, in another aspect, a method of determining the genotype of a cucumber plant of a line selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, comprising obtaining a sample of nucleic acids from said plant and detecting in said nucleic acids a plurality of polymorphisms. In particular embodiments, the method further comprises the step of storing the results of the step of detecting the plurality of polymorphisms on a computer readable medium.

Thus, a computer readable medium produced by obtaining a sample of nucleic acids from said plant, detecting in said nucleic acids a plurality of polymorphisms, and storing the results of the step of detecting the plurality of polymorphisms on a computer readable medium is another aspect of the invention.

In yet another aspect, the invention provides a method of producing cucumbers comprising: (a) obtaining a plant of the current invention, wherein the plant has been cultivated to maturity; and (b) collecting cucumbers from the plant.

DETAILED DESCRIPTION OF THE INVENTION

Figure 1:
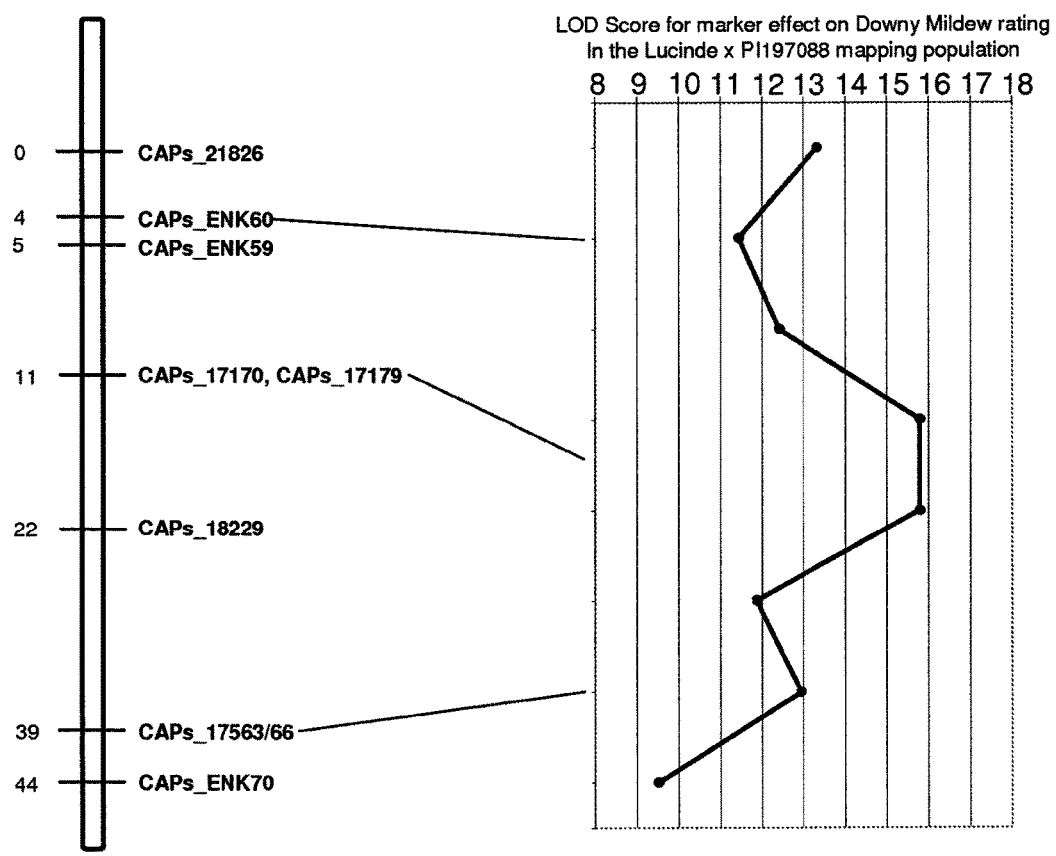
FIG. 1 depicts a genetic map (left) and LOD plot (right) for marker effects on Downy Mildew reaction in 148 F3 families from the cucumber L088 (Lucinde×PI197088) population. Lines between the genetic map and LOD plot provide reference positions for three of the markers to aid in comparisons of map position and LOD score.

The invention provides cucumber plants and in particular cucumber (*Cucumis sativus*) lines having resistance to Downy Mildew (DM). Such cucumber lines can be referred to as DM resistant cucumber varieties. Methods of producing DM resistant cucumber lines are also provided. Also disclosed herein are molecular markers that are linked to quantitative trait loci contributing to DM resistance, and $F_1$ hybrids of the DM resistant cucumber plants. Through use of the markers, one of skill in the art may increase the degree of DM resistance in cucumber or select plants for an increased predisposition for DM resistance. The QTLs identified in this manner may be combined with one or more other QTLs that also contribute to DM resistance, as desired.

The DM resistant cucumber plants of the present invention may bear one or more alleles conferring DM resistance that have been introduced into the cucumbers from a line designated PI197088 comprising the DM resistance, but otherwise comprising poor agronomic characteristics. The resulting DM resistant cucumber plants of the present invention surprisingly display elite agronomic traits in combination with DM resistance, while lacking deleterious traits.

DM resistant cucumber plants may have large leaves that form a canopy over the fruit. The vine is typically indeterminate and grown on trellises or the ground. DM resistant cucumber plants may have dark green, green, light green to yellow, and occasionally yellow to brown leaves. The leaves of the DM resistant cucumber plants vary in size, but typically are from about 200-250 mm in length and 150-200 mm in width, and are usually simple, alternate, palmate, and lobed.

The ripe fruit of DM resistant cucumber plants of the present invention can vary from light to medium green, or even dark green, and typically the color on an individual fruit varies from a lighter-colored blossom end to a darker colored stem-end. The color may be mottled with yellow speckles. The fruit of DM resistant cucumber is typically elongated and cylindrical with rounded or blunt ends, but may also be straight or curved, and is usually 25-30 cm in length at harvest maturity, although the fruit may be edible at 11-14 cm. The skin of the fruit is typically smooth, dull and thick; the skin may be tough or tender with a varied number of tubercules. The flesh of the fruit is usually cream colored, with or without stripes, and has a bitter-free taste.

As used herein, a "susceptible control cucumber plant" refers to a cucumber plant susceptible to Downy Mildew (DM susceptible) including commercially available and wild relatives of modern cucumber plants. In one aspect, the control cucumber plant is the variety MARAM, SMR58, or SPRINT 440. A "resistant control cucumber plant" may also be utilized when evaluating DM resistant cucumber varieties. In one embodiment, such a control is a cucumber plant that is not susceptible to DM, but is otherwise agriculturally undesirable, for example, variety PI197088. Similarly, some controls may have intermediate resistance, for example, controls with intermediate resistance to DM may be DMP21, GP14, LLP-1, or POINSETT 76. As described herein, a control cucumber line is grown under similar environmental conditions as the comparative cucumber line, according to the present disclosure.

As used herein, a "hybrid cucumber plant" includes a plant resulting directly or indirectly from crosses between populations, breeds or cultivars within the species *Cucumis sativus*. "Hybrid cucumber plant" as used herein also refers to plants resulting directly or indirectly from crosses between different varieties or genotypes.

As used herein, a "female parent" refers to a cucumber plant that is the recipient of pollen from a male donor line, which pollen successfully pollinates an egg. A female parent can be any cucumber plant that is the recipient of pollen. Such female parents can be male sterile, for example, because of genic male sterility, cytoplasmic male sterility, or because they have been subject to manual emasculation of the stamens. Genic or cytoplasmic male sterility can be manifested in different manners, such as sterile pollen, malformed or stamenless flowers, positional sterility, and functional sterility.

As used herein, "cytoplasmic male sterility" refers to plants that are not usually capable of breeding from self-pollination, but are capable of breeding from cross-pollination.

As used herein, "linkage" is a phenomenon wherein alleles on the same chromosome tend to segregate together more often than expected by chance if their transmission was independent.

As used herein, a "marker" is an indicator for the presence of at least one phenotype, genotype, or polymorphism. Markers include, but are not limited to, single nucleotide polymorphisms (SNPs), cleavable amplified polymorphic sequences (CAPS), amplified fragment length polymorphisms (AFLPs), restriction fragment length polymorphisms (RFLPs), simple sequence repeats (SSRs), insertions)/deletion(s) (INDEL(s)), inter-simple sequence repeats (ISSR), and random amplified polymorphic DNA (RAPD) sequences. A marker is preferably inherited in codominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both associated with DM resistance.

As used herein, a "desirable trait" or "desirable traits" that may be introduced into DM resistant cucumber plants by breeding may be directed to the cucumber fruit or the cucumber plant. Desirable traits to be introduced into cucumber plants and cucumber fruit may be independently selected. Desirable cucumber fruit traits that may be independently selected include, but are not limited to: fruit size, shape, color, surface appearance; seed number, seed size, locule number; pericarp thickness and toughness; taste, bitterness, the presence of tubercles, and shelf life. Desirable cucumber plant traits that may be independently selected include, but are not limited to; plant vigor, leaf shape, leaf length, leaf color, plant height, whether the plant is determinate or not, time to maturity, adaptation to field growth, adaptation to greenhouse growth, and resistance to one or more diseases or disease causing organisms such as *Verticillium* wilt, root knot nematodes, Tobacco Mosaic Virus, Cucumber scab, Anthracnose race 1, Powdery mildew (e.g. caused by *Erysiphe cichoracearum* or *Sphaerotheca fuliginea*), Target spot, Cucumber Mosaic Virus and *Fusarium* wilt. Any combination of desirable cucumber fruit traits, cucumber plant traits, or cucumber plant and fruit traits may be combined with a DM resistance trait.

DM resistance of a cucumber plant provided herein can potentially be defined as complete resistance or partial resistance. The DM resistance of a cucumber plant provided herein can be measured by any means available in the art.

In one aspect, DM resistance of a cucumber plant is determined using a disease rating of foliar chlorotic and/or necrotic lesion development after inoculation or infection with DM on cucumber leaves using a scale of symptoms of 0%, 10%, 20%, 30%, 40%, 50%, 60% and greater than about 60% lesion covering the leaf area. A disease rating of 0% indicates a completely resistant plant.

In another aspect, DM resistance is determined by obtaining disease ratings of symptom development after one or more rounds of inoculation or infection with DM on cucumber leaves and/or cotyledons. Resistance in a leaf test may be scored on the scale:

| Index Value | Symptoms |
| --- | --- |
| 1 | Absence of symptoms |
| 2 | Few small necrotic lesions without expansion |
| 3 | Few chlorotic and some necrotic lesions with limited expansion |
| 4 | Large expanding angular chlorosis with limited necrotic lesions |
| 5 | Large expanding angular chlorosis with expanding necrotic lesions |

Tests are evaluated once symptoms have developed on susceptible checks (e.g. cultivars Maram or SMR58). PI 197088 may be used as a "resistant" control; cv. Poinsett 76 may be used as a control to assess "intermediate" levels of resistance/susceptibility to *P. cubensis*. Three observations are made on each plot, one at each end and one in the middle. The mean disease index for each plot is calculated. These are averaged for all three replicates and the standard deviation is determined. The disease index ranges for the categories "Resistant," "Intermediate Resistant" and "Susceptible" are then determined. Varieties are generally trialed several times before a final disease resistance level determination is made. Scores of 1-5 indicate varying levels of resistance or susceptibility. A score of 1-2 after one or more rounds of inoculation or infection, and preferably two or more rounds of infection, indicates a resistant plant. A score of 3 after one or more rounds of inoculation or infection, preferably two or more rounds of infection, indicates a plant exhibiting intermediate resistance. A score of 4-5 indicates a susceptible plant. Scores on this 1-5 scale would correlate to a 1-9 scale where 1=1, 2=3, 3=5, 4=7, and 5=9.

In one aspect of the invention, a plant is assayed for DM resistance, partial resistance or susceptibility by image analysis of foliar tissue using about 3 leaves per plant captured in a digital image. The image analysis is conducted to determine the percentage of tissue damage and derive a disease rating. Image analysis software and methods used for quantifying visual differences in two or three dimensions are those set forth in Bright, 1987 (*J. Microscopy* 148:51-87) and Bickmore et al., 1999 (*Geol. Mat. Res.* 1(5):1-19). With respect to image analysis: "very resistant" exhibits between about 0% and 5% leaf area symptoms of chlorotic and/or necrotic lesions; "resistant" is between about 1% and 20% of the leaf area having symptoms of chlorotic and/or necrotic lesions; "substantially resistant" is between about 20% and 30% of the leaf area having symptoms of chlorotic and/or necrotic lesions; "mid-resistant" is between 40% and 50% of the leaf area having symptoms of chlorotic and/or necrotic lesions; "partially resistant" is less than or equal to about 50% of the leaf area having symptoms of chlorotic and/or necrotic lesions; "mid-susceptible" is between about 50% and 60% of the leaf area having symptoms of chlorotic and/or necrotic lesions; and "susceptible" is between about 60% and 100% of the leaf area having symptoms of chlorotic and/or necrotic lesions. A resistant plant can be characterized by other aspects as set forth herein, or by the use of other means, such as quantitative PCR to determine the level of infection.

Cucumber lines having DM resistance, or partial resistance, demonstrate a reduced level of symptoms relative to a non-resistant control cucumber line after inoculation or infection with DM. The level of symptoms can be used as an indicator of DM resistance. Disease symptoms measured can be any disease symptoms associated with DM infection. Symptoms can be selected from the group consisting of leaf blisters, necrosis, soft fruits, mosaic, chlorotic veins, chlorotic leaf spots, chlorotic and/or light green mosaic on leaves, fruit lesions, or combinations thereof. In one aspect, a DM resistant cucumber line demonstrates a reduction of foliar symptoms of chlorotic and/or necrotic lesions of at least, or greater than, 10%, 20%, 25%, 30%, 40%, 50%, 60%, 70%, 75%, 80%, 85%, 90%, 95%, or 98% relative to a non-resistant control cucumber line. In other aspects, the leaves of a DM resistant cucumber plant demonstrate less than 15%, or less than 10%, or less than 5%, or less than 2% symptomatic area when exposed to DM. In another aspect, the cucumber plant belongs to a cucumber variety or cultivar, and in another aspect, the cucumber plant is an inbred cucumber plant.

In another aspect, the cucumber plants and varieties provided herein demonstrates little or no symptoms of chlorotic and/or necrotic lesions after inoculation or infection with DM. In some aspects, a DM resistant cucumber plant demonstrates symptoms of chlorotic and/or necrotic lesions on less than 10%, 9%, 8%, 7%, 6%, 5%, 4%, 3% 2%, or 1% of the cucumber leaf surface.

DM resistant cucumber plants may exhibit a delay in the onset of symptoms of chlorotic and/or necrotic lesions relative to a non-resistant control cucumber plant. In some embodiments, the DM resistant cucumber plants exhibit a delay of 1, 2, 3, 4, 5, 6, 7, 8, 9, 10, 11, 12, 13, 14, or more days in the onset of symptoms of chlorotic and/or necrotic lesions relative to a control cucumber plant. In other embodiments, the DM resistant cucumber plants exhibit a delay of at least 7 or more days, 10 or more days, or 14 or more days in the onset of symptoms of chlorotic and/or necrotic lesions relative to a control cucumber plant.

In one aspect, the cucumber plant is a seedling at the time of inoculation or infection. In some aspects, the cucumber plant is a seedling at the 4, 5, 6, 7, or 8 leaf stage of development when inoculated. In one aspect, disease symptoms can be measured at any time after pathogenic challenge of a cucumber plant. In other aspects, symptoms can be measured 2, 3, 4, 5, 6, 7, 8, 9, 10, 11, 12, 13, 14, 15, 16, 17, 18, 19, 20, 21, or more days after inoculation. In another aspect, the cucumber plant is any age of plant at the time of inoculation or infection.

In another aspect, disease symptoms can be observed after DM challenge of an entire plant or a part thereof, for example, a plant cutting.

DM resistant cucumber plants of the present invention may exhibit an increase in fruit yield after inoculation or infection with DM relative to a control cucumber plant inoculated with DM. In one aspect, the resistant cucumber plants exhibit a 2%, 5%, 10%, 15%, 20% or more increase in fruit yield, based upon the total mass, number, or total volume of fruit, relative to a control cucumber plant after one or more rounds of inoculation or infection with DM.

The present invention provides for and includes cucumber plants that exhibit resistance to one or more races of DM. In some embodiments, the cucumber plants of the present invention exhibit resistance to 1, 2, 3, 4, 5, 6, 7, 8, 9, 10, or more races of DM.

The present invention provides for a seed of a cucumber plant capable of producing a plant having DM resistance. In one aspect, the cucumber plant can be an open-pollinated variety, a hybrid parent inbred line, or a male sterile line. In another aspect, the invention provides seed of a cucumber plant capable of producing a hybrid cucumber plant having DM resistance.

The cucumber plants of the present invention can be cucumber lines adapted for greenhouse cucumber production or for field cucumber production. In one aspect, the cucumber plants of the present invention are adapted for greenhouse cucumber production.

The present invention also provides a hybrid cucumber having DM resistance. In another aspect, the present invention provides a hybrid cucumber exhibiting DM resistance after inoculation or infection with DM.

Commercially valuable cucumber plants represent one aspect of the present invention. In one aspect, certain cucumber traits, including, for example, fruit size, shape, color, weight, taste and fruit yield may be important to the commercial value of the crop. Fruit size, and shape, may be of particular interest if the cucumbers are grown for processing such as pickling. The present invention provides for a cucumber plant that produces a cucumber fruit having a length of about, or greater than about, 11, 12, 13, or 14 cm. In another aspect, a cucumber plant of the present invention produces a cucumber fruit having a length between about 11 and 13 cm, 12 and 14 cm, and 11 and 14 cm.

In some aspects, a cucumber plant of the present invention may produce a cucumber fruit having a weight at harvest of about or greater than about 80, 85, 90, 95, 100, 105, 110, 115, 120, and 125 grams. In other aspects, a cucumber plant of the present invention produces a cucumber fruit having a weight at harvest between about 80 and about 125 grams, about 90 and about 115 grams, about 100 and about 120 grams, about 90 and about 125 grams, about 95 and about 125 grams, about 100 and about 125 grams, or between about 115 and about 125 grams. Fruit weight is measured by weighing individual cucumber fruit on a scale.

Mature cucumber fruit produced by DM resistant plants of the present invention may have a diameter from about 10, 11, 12, 13, or 14 mm or larger. In some embodiments the diameter of the cucumber fruit may be from about 10 to about 11 mm, or from about 10 to about 12 mm, or from about 11 to about 13 mm, or from about 12 to about 14 mm, or from about 13 to about 14 mm.

A cucumber fruit attribute such as shape, weight, or size can be measured or evaluated at a variety of times. In one aspect, an attribute is measured following growth in a growth chamber. In another aspect, an attribute is measured at the time of harvest. In yet another aspect, an attribute is measured after storage of the cucumber fruit at ambient conditions for one day, two days, three days, four days, five days, six days, seven days, eight days, nine days, ten days, eleven days, twelve days, thirteen days, two weeks, three weeks, four weeks, or five weeks after harvest.

In one embodiment, a cucumber fruit from a cucumber plant having DM resistance has an overall fruit quality rating of 1, 3, 5, 7, or 9, where fruit quality is measured by visual inspection, with a scale ranging from 1=excellent through 9=poor: Rating 1=Excellent; 3=Above average; 5=Average; 7=Below average; 9=Poor; compared to the standard commercial hybrid grown in the area. Fruit Quality relates to fruit color, fruit shape, fruit length and diameter.

A further aspect of the invention relates to tissue cultures of the cucumber plants described herein. As used herein, the term "tissue culture" indicates a composition comprising isolated cells of one or more types, or a collection of such cells organized into parts of a plant. Tissue culture includes, but is not limited to, compositions comprising protoplasts and calli. Tissue culture also includes, but is not limited to, compositions comprising plant cells that are present in intact plant tissues, or parts of plants, such as embryo, leaf, peduncle, pedicel, anther, meristem, tip and segments of root, stump and stem, explants, and the like. In one aspect, a tissue culture comprises embryos, protoplasts, meristematic cells, pollen, leaves, anthers or cells derived from immature tissues of these plant parts. Means for preparing and maintaining plant tissue cultures are well known in the art. Examples of processes of tissue culturing and regeneration of cucumber are described in, for example, Fillatti et al., 1987 (*Bio/Technology*, 5:726-730). In some aspects, tissue culture of the cucumber plants described herein relates to the culture of protoplasts, calli, or plant cells, that are isolated from, or present in, intact parts of the DM resistant plants described herein. In another aspect, tissue culture refers to the culture of protoplasts, calli, or plant cells, that are isolated from, or present in, intact parts of plants of one or more DM resistant cucumber plant lines selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, and DM resistant progeny thereof, including those produced by crosses or backcrosses. In yet another aspect, tissue culture of the cucumber plants described herein relates to the culture of protoplasts, calli, or plant cells, that are isolated from, or present in, intact parts of the DM resistant plants described herein.

Once DM resistant plants are produced, the plants themselves can be cultivated in accordance with conventional procedures. DM resistant progeny may be obtained through sexual reproduction. The seeds resulting from sexual reproduction can be recovered from the fruit of DM resistant plants and planted or otherwise grown as a means of propagation. DM resistant progeny may also be obtained from DM resistant plants through asexual reproduction. Protoplast or propagules (e.g., cuttings, scions or rootstocks) can be recovered from DM resistant plants or parts thereof and may be employed to propagate DM resistant plants.

The present invention also provides for and includes a container of cucumber seeds in which cucumber plants grown from greater than 50% of the seeds have resistance or partial resistance to DM. In another aspect, cucumber plants grown from greater than 55%, 65%, 75%, 85%, 90%, 95%, 98%, or 99% of the cucumber seeds in the container have DM resistance. Another aspect of the invention relates to seeds from a cucumber plant selected from the group consisting of all deposited lines as referred to previously, and DM resistant progeny thereof, wherein cucumber plants grown from about 50%, or greater than 50%, of the seeds have resistance or partial resistance to DM.

The container of cucumber seeds can contain any number, weight or volume of seeds. For example, a container can contain about, or greater than about, 10, 25, 50, 200, 400, 700, 1000, 2000, 3000, or more seeds. In another aspect, a container can contain about, or greater than about, 1 gram, 5, 10, 15, 25, 100, 250, 500, or 1,000 grams of seeds. Alternatively, the container can contain about or at least, or greater than, about 1 ounce, 2, 4, 8, 10 ounces, 1 pound, 2, 4, 8, 12 pounds or more of seeds.

Containers of cucumber seeds can be any container available in the art. For example, a container can be a box, a bag, a packet, a pouch, a tape roll, a foil, a pail, or a tube.

The present invention includes and provides for a container of cucumber fruit from cucumber plants having DM resistance. In one aspect, the container contains about 2, 5, 10, 20, 40, 80, 100, or more cucumber fruit. In yet another aspect, the present invention provides a cucumber vine having cucumber fruit from a plant having resistance to DM.

One aspect of the invention relates to dried, or otherwise processed, cucumber fruit, produced by a cucumber plant having a genome that comprises at least one genetic locus giving rise to DM resistance when expressed in a cucumber plant. Processed cucumber fruit includes, but is not limited to fruit pulp, stewed cucumbers, canned, pickled, minced, sliced, or crushed cucumber fruit. In some aspects, the dried, pickled, or otherwise processed cucumber fruit, is the fruit of a cucumber plant selected from one or more of the group consisting of all deposited lines as referred to previously, and DM resistant progeny thereof.

The present invention provides for an inbred cucumber plant having resistance to DM, wherein the resistance is exhibited when the plant is in contact with DM. In one aspect, the inbred cucumber plant is derived from accession PI197088.

The present invention includes and provides for *C. sativus* plants having at least one allele for a DM resistance trait. The DM resistant cucumber plants can be either heterozygous or homozygous for the DM resistance trait. In one embodiment, the DM resistant trait can be linked to variations in a single gene (e.g., linked to one or more alleles of a single gene). In another embodiment, the DM resistance trait can be linked to variations at one or one or more quantitative trait loci (QTL). In a yet another embodiment, the DM resistant cucumber plants are homozygous for the DM resistance trait.

The present invention provides for a *C. sativus* cucumber plant having a genome that comprises at least one genetic locus that provides DM resistance from a non-*C. sativus* plant. In some aspects, the DM resistant cucumber plant is selected from the group consisting of all deposited lines as referred to previously, and DM resistant progeny thereof. In one aspect, the genetic locus derived from a DM resistant cucumber plant can be identified using genetic markers.

The present invention provides for a DM resistant *C. sativus* cucumber plant having less than or equal to 50% of its genome derived from a non-*C. sativus* DM resistant plant. In another aspect, a DM resistant *C. sativus* cucumber plant can have 50%, 25%, 12.5%, 6%, 3% or less nuclear DNA derived from a DM resistant non-*C. sativus* plant. In other aspects, a DM resistant *C. sativus* cucumber plant can have 50%, 25%, 12.5%, 6% or 3% or less nuclear DNA derived from another member of the *Cucumis* genus that is DM resistant.

The present invention provides progeny of cucumber plants having resistance to DM. As used herein, progeny include not only, without limitation, the products of any cross (be it a backcross or otherwise) between two plants, but all progeny whose pedigree traces back to the original cross. In one aspect of the present invention, the progeny contain about 50%, 25%, 12.5% or less nuclear DNA from a DM resistant cucumber plant and expresses the genetic material that provides DM resistance.

One embodiment of the present invention provides for a DM resistant cucumber plant that contains a genetic marker linked to one or more DM resistance locus. By "DM resistance locus" is meant a locus that contributes to DM resistance either alone or in combination with one more other DM resistance locus. By "contributes to Downy Mildew resistance" it is meant that the degree of Downy Mildew resistance is increased in the corresponding plant, either when the locus is alone or in combination with one or more other locus.

In one embodiment of the invention, a marker linked to one or more DM resistance loci includes one or more of the following: CAPs_21826, CAPs_ENK60, CAPs_ENK59, CAPs_17170, CAPs_17179, CAPs_18229 CAPs_17563/66, and CAPs_ENK70. In another embodiment of the invention, the assayed markers linked to one or more DM resistance loci include each of the following: CAPs_ENK60, CAPs_17170, and CAPs_17563/66.

As used herein, linkage of two nucleic acid sequences, including a nucleic acid marker sequence and a nucleic acid sequence of a genetic locus imparting a desired trait such as DM resistance, may be genetic or physical or both. In one aspect of the invention, the nucleic acid marker and genetic locus conferring DM resistance are genetically linked, and exhibit a LOD score of greater than 2.0, as judged by interval mapping for the DM resistance trait based on maximum likelihood methods described by Lander and Botstein, 1989 (*Genetics,* 121:185-199), and implemented in the software package MAPMAKER (e.g. Lander et al., *Genomics* 1:174-181, (1987); default parameters). In other embodiments, the marker and region conferring DM resistance are genetically linked and exhibit a LOD score of greater than 3.0, or a LOD score of greater than 6.0, 9.0, 12.0, 15.0, or 18.0. In one embodiment, the marker and region contributing to DM resistance are genetically linked and exhibit a LOD score of between about 14 and about 20.

In another aspect, the nucleic acid marker is genetically linked at a distance of between about 0 and about 50 centimorgans (cM) to the DM resistance locus. In other embodiments, the distance between the nucleic acid marker and the DM resistance locus is between about 0 and about 35 cM, or between about 0 and about 25 cM, or between about 0 and about 15 cM, or between about 0 and about 10 cM, or between about 0 and about 5 cM, including less than about 4, 3, 2 or 1 cM.

In another aspect, the nucleic acid molecule may be physically linked to a DM resistance locus. In some aspects, the nucleic acid marker specifically hybridizes to a nucleic acid molecule having a sequence that is within about 30 Mbp, or about 20 Mbp, or about 15 Mbp, or about 10 Mbp, or about 5 Mbp of a DM resistance locus.

As used herein, two nucleic acid molecules are said to be capable of hybridizing to one another if the two molecules are capable of forming an anti-parallel, double-stranded nucleic acid structure. Conventional stringency conditions are described by Sambrook et al., *Molecular Cloning, A Laboratory Manual*, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. In some embodiments, hybridization conditions can be high, moderate or low stringency conditions. Preferred conditions include those using 50% formamide, 5.0×SSC, 1% SDS and incubation at 42° C. for 14 hours, followed by a wash using 0.2×SSC, 1% SDS and incubation at 65° C.

The specificity of hybridization can be affected by post-hybridization washes. For example, the salt concentration in the wash step can be selected from a low stringency of about 2.0×SSC at 50° C. to a moderate stringency of about 1.0×SSC at 50° C. to a high stringency of about 0.2×SSC at 50° C. In addition, the temperature in the wash step can be increased from low stringency conditions at room temperature, about 22° C., to moderate stringency conditions at about 50° C., to high stringency conditions at about 65° C. Both temperature and salt concentration may be varied, or either the temperature or the salt concentration may be held constant while the other variable is changed. In some aspects, the wash step can be performed for 5, 10, 15, 20, 25, 30, or more minutes. In another aspect, the wash step is performed for about 20 minutes. In yet another aspect, the wash step can be repeated 1, 2, 3, 4, or more times using the selected salt concentration, temperature, and time. In another aspect, the wash step is repeated twice.

A genetic marker profile of a plant may be predictive of the agronomic traits of a hybrid produced using that inbred. For example, if an inbred plant of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data are disclosed in U.S. Pat. No. 5,492,547, the disclosure of which is specifically incorporated herein by reference in its entirety. Such predictions may be made using any suitable genetic marker, for example, SSRs, INDELs, RFLPs, AFLPs, SNPs, ISSRs, or isozymes.

Additional markers, such as SSRs, AFLP markers, RFLP markers, RAPD markers, phenotypic markers, SNPs, isozyme markers, or microarray transcription profiles that are genetically linked to or correlated with DM resistance can be utilized (Walton, *Seed World* 22-29 (July, 1993); Burow and Blake, *Molecular Dissection of Complex Traits*, 13-29, Eds. Paterson, CRC Press, New York (1988)). Methods to isolate such markers are known in the art. For example, locus-specific SSRs can be obtained by screening a cucumber genomic library for SSRs, sequencing of "positive" clones, designing primers which flank the repeats, and amplifying genomic DNA with these primers.

The genetic linkage of marker molecules to DM resistance can be established by a gene mapping model such as, without limitation, the flanking marker model, and the interval mapping, based on maximum likelihood methods described by Lander and Botstein, 1989 (*Genetics*, 121:185-199), and implemented in the software package MAP-MAKER.

A maximum likelihood estimate (MLE) for the presence of a marker is calculated, together with an MLE assuming no trait effect, to avoid false positives. A $\log_{10}$ of an odds ratio (LOD) is then calculated as: LOD=$\log_{10}$ (MLE for the presence of a trait (MLE given no linked trait)).

The LOD score essentially indicates how much more likely the data are to have arisen assuming the presence of a resistance allele rather than in its absence. The LOD threshold value for avoiding a false positive with a given confidence, say 95%, depends on the number of markers and the length of the genome. Graphs indicating LOD thresholds are set forth in Lander and Botstein (1989), and further described by Ars and Moreno-Gonzalez, *Plant Breeding*, Hayward, Bosemark, Romagosa (eds.) Chapman & Hall, London, pp. 314-331 (1993).

Selection of appropriate mapping or segregation populations is important in trait mapping. The choice of appropriate mapping population depends on the type of marker systems employed (Tanksley et al., Molecular mapping plant chromosomes. Chromosome structure and function: Impact of new concepts J. P. Gustafson and R. Appels (eds.), Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

As used herein, the progeny include not only, without limitation, the products of any cross (be it a backcross or otherwise) between two plants, but all progeny whose pedigree traces back to the original cross. Specifically, without limitation, such progeny include plants that have 50%, 25%, 12.5% or less nuclear DNA derived from one of the two originally crossed plants. As used herein, a second plant is derived from a first plant if the second plant's pedigree includes the first plant.

The present invention provides a genetic complement of the cucumber lines described herein. Further provided is a hybrid genetic complement, wherein the complement is formed by the combination of a haploid genetic complement from elite inbred cucumber lines described herein and another haploid genetic complement. Means for determining such a genetic complement are well-known in the art.

As used herein, the phrase "genetic complement" means an aggregate of nucleotide sequences, the expression of which defines the phenotype of a plant, such as a *C. sativus* cucumber plant or a cell or tissue of that plant. By way of example, a *C. sativus* cucumber plant is genotyped to determine a representative sample of the inherited markers it possesses. Markers are preferably inherited in codominant fashion so that the presence of both alleles at a diploid locus is readily detectable, and they are free of environmental variation, i.e., their heritability is close to, or equal to, 1. This genotyping is preferably performed on at least one generation of the descendant plant for which the numerical value of the trait or traits of interest are also determined. The array of single locus genotypes is expressed as a profile of marker alleles, two at each locus for a diploid plant. The marker allelic composition of each locus can be either homozygous or heterozygous. Homozygosity is a condition where both alleles at a locus are characterized by the same conditions of the genome at a locus (e.g., the same nucleotide sequence). Heterozygosity refers to different conditions of the genome at a locus. Potentially any type of genetic marker could be used, for example, simple sequence repeats (SSRs), insertion/deletion polymorphism (INDEL), restriction fragment length polymorphisms (RFLPs), amplified fragment length polymorphisms (AFLPs), single nucleotide polymorphisms (SNPs), and isozymes.

Considerable genetic information can be obtained from a completely classified $F_2$ population using a codominant marker system (Mather; Measurement of Linkage in Heredity: Methuen and Co., (1938)). An $F_2$ population is the first generation of self or sib pollination after the hybrid seed is produced. Usually a single $F_1$ plant is self or sib pollinated to generate a population segregating for the nuclear-encoded genes in a Mendelian (1:2:1) fashion.

In contrast to the use of codominant markers, using dominant markers often requires progeny tests (e.g., $F_3$ or back cross self families) to identify heterozygous individuals. The information gathered can be equivalent to that obtained in a completely classified $F_2$ population. This procedure is, however, often prohibitive because of the cost and time involved in progeny testing. Progeny testing of $F_2$ individuals is often used in map construction where error is associated with single plant phenotyping, or when sampling the plants for genotyping affects the ability to perform accurate phenotyping, or where trait expression is controlled by a QTL. Segregation data from progeny test populations (e.g., $F_3$ or backcrossed or selfed families) can be used in trait mapping. Marker-assisted selection can then be applied to subsequent progeny based on marker-trait map associations ($F_2$, $F_3$), where linkage has not been completely disassociated by recombination events (i.e., maximum disequilibrium).

Recombinant inbred lines (RILs) (genetically related lines; usually >$F_5$) can be used as a mapping population. RILs can be developed by selfing F2 plants, then selfing the resultant F3 plants, and repeating this generational selfing process, thereby increasing homozygosity. Information obtained from dominant markers can be maximized by using RILs because all loci are homozygous or nearly so. Under conditions of tight linkage (i.e., about <10% recombination), dominant and co-dominant markers evaluated in RIL populations provide more information per individual than either marker type in backcross populations (e.g. Reiter et al., 1992; *Proc. Natl. Acad. Sci.* (*U.S.A.*) 89:1477-1481). However, as the distance between markers becomes larger (i.e., loci become more independent), the information in RIL populations decreases dramatically when compared to codominant markers.

Backcross populations can be utilized as mapping populations. A backcross population (BC) can be created by crossing an $F_1$ to one of its parents. Typically, backcross populations are created to recover the desirable traits (which may include most of the genes) from one of the recurrent parental (the parent that is employed in the backcrosses) while adding one or a few traits from the second parental, which is often referred to as the donor. A series of backcrosses to the recurrent parent can be made to recover most of the recurrent parent's desirable traits. Thus a population is created consisting of individuals nearly like the recurrent parent, wherein each individual carries varying amounts or a mosaic of genomic regions from the donor parent. Backcross populations can be useful for mapping dominant markers particularly if all loci in the recurrent parent are homozygous and the donor and recurrent parent have contrasting polymorphic marker alleles (Reiter et al., 1992; *Proc. Natl. Acad. Sci.* (*U.S.A.*) 89:1477-1481).

Information obtained from backcross populations using either codominant or dominant markers is less than that obtained from completely classified $F_2$ populations because recombination events involving one, rather than two, gametes are sampled per plant. Backcross populations, however, are more informative (at low marker saturation) when compared to RILs as the distance between linked loci increases in RIL populations (i.e., about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the loci polymorphic between the parentals are expected to segregate in the highly homozygous NIL population. Those loci that are polymorphic in a NIL population, however, are likely to be linked to the trait of interest.

Bulk segregant analysis (BSA) is a method developed for the rapid identification of linkage between markers and traits of interest (Michelmore, et al., 1991; *Proc. Natl. Acad. Sci.* (*U.S.A.*) 88:9828-9832). In BSA, two bulk DNA samples are drawn from a segregating population originating from a single cross. These bulk samples contain individuals that are identical for a particular trait (e.g., resistant or susceptible to a particular pathogen) or genomic region but arbitrary at unlinked regions (i.e., heterozygous). Regions unlinked to the target trait will not differ between the bulked samples of many individuals in BSA.

In another aspect, the present invention provides a method of producing a DM resistant cucumber plant comprising: (a) crossing a cucumber line having DM resistance with a second cucumber line lacking DM resistance to form a segregating population; (b) screening the population for resistance to DM; and (c) selecting one or more members of the population having said DM resistance. In one aspect, the cucumber line having DM resistance is crossed with the second cucumber line for at least two generations (e.g., creating either an $F_2$ or $BC_1S_1$ population). In another aspect, plants are identified as DM resistant prior to crossing. In one aspect, plants can be selected on the basis of partial or complete resistance to DM. In one aspect, the segregating population is self-crossed and the subsequent population is screened for resistance.

In another aspect, the present invention provides a method of introgressing DM resistance into a cucumber plant comprising: (a) crossing at least a first cucumber line having DM resistance with a second cucumber line to form a segregating population; (b) screening said population for resistance to DM; and (c) selecting at least one member of said population exhibiting DM resistance. In one aspect, the cucumber line having DM resistance is crossed with the second cucumber line for at least two generations (e.g., creating either an $F_2$ or $BC_1S_1$ population). In another aspect, plants are identified as DM resistant prior to crossing. In one aspect, the segregating population is self-crossed and the subsequent population is screened for resistance.

Cucumber plants generated using a method of the present invention can be part of or generated from a breeding program. The choice of breeding method depends on the mode of plant reproduction, the heritability of the trait(s) being improved, and the type of cultivar used commercially (e.g., $F_1$ hybrid cultivar, pure line cultivar, etc). Selected, non-limiting approaches for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, fruit size, fruit quality, and/or fruit yield will generally dictate the choice.

For highly heritable traits, a choice of superior individual plants evaluated at a single location will be effective, whereas for traits with low heritability, selection should be based on statistical analyses (e.g., mean values) obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates as parents for new commercial cultivars; those still deficient in traits may be used as parents for hybrids, or to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated self or sib pollinating and selection, producing many new genetic combinations.

The development of new cucumber lines requires the development and selection of cucumber varieties, the crossing of these varieties and selection of superior hybrid crosses. The hybrid seed can be produced by manual crosses between selected male-fertile parents or by using male sterility systems. Hybrids can be selected for certain single gene traits such as flower color, seed yield or herbicide resistance that indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes into parent lines. These lines are used to produce new cultivars. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is performed. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding and cross breeding have been used to transfer genes for a simply inherited, highly heritable trait into a desirable homozygous cultivar or inbred line, which is the recurrent parent. The source of the trait to be transferred is called the donor parent. The resulting plant obtained from a successful backcrossing program is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. After multiple backcrossing generations with selection, the resulting line is expected to have the attributes of the recurrent parent (e.g., cultivar) and the desirable trait transferred from the donor parent.

Cross breeding or backcross breeding of a DM resistant cucumber plant may be conducted where the other parent (second cucumber plant) is DM resistant or the other parent is not DM resistant.

Cucumber plants generated of the invention may be generated using a single-seed descent procedure. The single-seed descent procedure, in the strict sense, refers to planting a segregating population, then selecting one plant in this and each subsequent generation to self and create the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several available reference books (e.g., Fehr, *Principles of Cultivar Development* Vol. 1, pp. 2-3 (1987)).

In one aspect of the present invention, the source of DM resistance trait for use in a breeding program is derived from a plant selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, and DM resistant progeny thereof. In another aspect, the source of the DM resistance trait for use in a breeding program is not derived from a plant selected from the group consisting of ASL147-2027, EUR154-1012GY, EUR154-1021GY, GSP33-1094GY, GPN33-1093GY, 03/8020-

20_TUP03_DMFL_1, 03/8024-19_TUP03_DMFL_1, and 03/8039-5_TUP03_DMFL_1, and DM resistant progeny thereof.

Another aspect of the invention is directed to an inbred cucumber plant having resistance to DM, wherein said resistance is exhibited when said plant is in contact with said DM, and wherein said cucumber plant is not derived from a plant selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1. Also included in the invention is a cucumber plant having a genome, wherein said genome comprises a genetic locus conferring resistance to DM, wherein said genetic locus contains one or more genetic markers linked to said genetic locus conferring resistance to DM, and wherein said cucumber plant is not accession PI197088.

In another aspect, additional sources of DM resistance for use in a breeding program can be identified by screening cucumber germplasm for resistance to DM. In a yet another aspect, cucumber plants can be screened for DM resistance by identifying germplasm exhibiting reduced disease symptoms relative to a control cucumber plant after inoculation or infection. In one aspect, cucumber plants can be screened for resistance to DM using a disease screen such as a field or greenhouse screen as described in Example 1 or Example 2.

In another aspect, additional sources of DM resistance for use in a breeding program can be identified by screening with one or more molecular markers linked to a genetic locus conferring resistance to DM, such as those identified herein.

In another aspect, additional sources of DM resistance for use in a breeding program can be identified by a combination of screening cucumber plants for reduced disease symptoms then screening with one or more molecular markers linked to a genetic locus contributing to resistance to DM.

In another aspect, cucumber lines having DM resistance can be used in breeding programs to combine DM resistance with additional traits of interest. In one aspect, DM resistance can be combined with any additional trait, including disease resistant traits, yield traits, and fruit quality traits. For example, breeding programs can be used to combine the DM resistance trait with alleles that contribute to size and shape in cucumber fruit. Breeding programs can also be used to combine DM resistance with one or more disease resistant traits. Such disease resistant traits include, without limitation, resistance to: *Verticillium* wilt, root knot nematodes, Tobacco Mosaic Virus, Cucumber scab, Powdery mildew, Target spot, Cucumber Mosaic Virus, and *Fusarium* wilt. In another aspect, the traits that are combined can be co-inherited in subsequent crosses.

The present invention also provides for parts of the DM resistant cucumber plants produced by a method of the present invention. Parts of cucumber plants, without limitation, include plant cells or parts of plant cells, seed, endosperm, meristem, flower, anther, ovule, pollen, fruit, flowers, stems, roots, stalks or leaves, scions, and root stocks. Plant parts also include the parts of a cucumber fruit, which include the placenta, columella and pericarp. In one embodiment of the present invention, the plant part is a seed.

The invention further provides for parts of a cucumber plant having a genome, that comprises at least one genetic locus giving rise to DM resistance in the cucumber plant. In another embodiment, parts of cucumber plants are derived from a cucumber plant selected from the group consisting of all deposited lines and DM resistant progeny thereof. In accordance with one aspect of the present invention, the physiological and morphological characteristics of deposited lines ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1 are set forth in Tables 1-8 below.

TABLE 1

Physiological and Morphological Characteristics of Line ASL147-2027 Mo.

| | CHARACTERISTIC | ASL147-2027 |
|---|---|---|
| 1. | Type | Cucumber |
| | Predominate Usage | Slicing |
| | Predominate Culture | Outdoor |
| | Area of Best Adaptation in USA | Most Areas |
| 2. | Maturity | |
| | Days from Seeding to Market | 50-55 |
| 3. | Plant | |
| | Habit | Vine |
| | Growth | Indeterminate |
| | Sex | Monoecious |
| | Flower Color | Yellow |
| 4. | Fruit at Edible Maturity | |
| | Fruit Neck Shape | Not Necked |
| | Fruit Tapering | Ends Blunt or Rounded |
| | Skin Thickness | Thick |
| | Skin Ribs | Ribbed |
| | Skin Toughness | Tough |
| | Skin Luster | Dull |
| | Spine Color | White |
| | Spine Quality | Coarse |
| | Spine Density | Few |
| | Flavor | Bitterfree |
| 5. | Insect Resistance | |
| | Aphid (*Aphis gossypii*) | Susceptible |

TABLE 2

Physiological and Morphological Characteristics of Line EUR154-1012 GY.

| | CHARACTERISTIC | EUR 154-1012 GY |
|---|---|---|
| 1. | Type | Cucumber |
| | Predominate Usage | Fresh |
| | Predominate Culture | Greenhouse |
| | Area of Best Adaptation in USA | Spain |
| 2. | Maturity | |
| | Days from Seeding to Market | 60-65 |
| 3. | Plant | |
| | Habit | Vine |
| | Growth | Indeterminate |
| | Sex | Gynoecious |
| | Flower Color | Yellow |
| 4. | Stem | |
| | Length | 150-200 cm |
| | Internode Length | 5-8 cm |
| | Stem Form | Grooved-Ridged |
| 5. | Fruit at Edible Maturity | |
| | Length | 30-32 cm |
| | Diameter at Medial | 45-50 mm |
| | Weight | 300-400 gm |
| | Skin Color | Medium green |
| | Yellowish Blossom End Strips | No |
| | Predominant Color at Stem End | Uniform green |
| | Predominant Color at Blossom End | Uniform green |
| | Fruit Neck Shape | Medium |
| | Fruit Tapering | Rounded |
| | Stem End Cross Section | rd |
| | Medial Cross Section | rd |
| | Blossom End Cross Section | rd |
| | Skin Thickness | Thin |
| | Skin Ribs | Ribbed |
| | Skin Toughness | Low |
| | Skin Luster | Shiny |

TABLE 2-continued

Physiological and Morphological Characteristics of Line EUR154-1012 GY.

| | CHARACTERISTIC | EUR 154-1012 GY |
|---|---|---|
| | Spine Color | White |
| | Spine Quality | Fine |
| | Spine Density | Very low |
| | Tubercles (Warts) | No |
| | Flavor | Bitterfree |
| 6. | Fruit at Harvest Maturity | |
| | Length | 35-37 cm |
| | Diameter at Medial | 50-60 mm |
| | Color | Yellow |
| | Color Pattern | Striped |
| | Surface | Smooth |
| | Netting | Slight or none |
| | Fruit Set | Normally without seeds |
| 7. | Seeds | |
| | No. per Fruit | 30-80 |
| | Per 1,000 Seeds | 30-35 gm |
| 8. | Disease Resistance | |
| | Cucumber Scab (Gumosis) (*Cladosporium cucumerinum*) | |
| | Downy Mildew | Resistant |
| | Powdery Mildew (*Erysiphe cichoracearum*) | Resistant |
| | Cucumber Mosaic Virus | Susceptible |
| | Cucumber Vein Yellowing Virus | Susceptible |
| | Cucumber yellow Stunted Disorder Virus | Intermediate resistance |
| 9. | Insect Resistance | |
| | Aphid (*Aphis gossypii*) | Susceptible |

TABLE 3

Physiological and Morphological Characteristics of Line EUR 154-1021 GY.

| | CHARACTERISTIC | EUR 154-1021 GY |
|---|---|---|
| 1. | Type | Cucumber |
| | Predominate Usage | Fresh |
| | Predominate Culture | Greenhouse |
| | Area of Best Adaptation in USA | Spain |
| 2. | Maturity | |
| | Days from Seeding to Market | 60-65 |
| 3. | Plant | |
| | Habit | Vine |
| | Growth | Indeterminate |
| | Sex | Gynoecious |
| | Flower Color | Yellow |
| 4. | Stem | |
| | Length | 150-200 cm |
| | Internode Length | 50-80 mm |
| | Stem Form | Grooved-Ridged |
| 5. | Fruit at Edible Maturity | |
| | Length | 30-32 cm |
| | Diameter at Medial | 45-50 mm |
| | Weight | 300-400 gm |
| | Skin Color | Medium green |
| | Yellowish Blossom End Strips | No |
| | Predominant Color at Stem End | Uniform green |
| | Predominant Color at Blossom End | Uniform green |
| | Fruit Neck Shape | Not necked |
| | Fruit Tapering | Rounded |
| | Stem End Cross Section | rd |
| | Medial Cross Section | rd |
| | Blossom End Cross Section | rd |
| | Skin Thickness | Thin |
| | Skin Ribs | Ribbed |
| | Skin Toughness | Low |
| | Skin Luster | Shiny |
| | Spine Color | White |

TABLE 3-continued

Physiological and Morphological Characteristics of Line EUR 154-1021 GY.

| | CHARACTERISTIC | EUR 154-1021 GY |
|---|---|---|
| | Spine Quality | Fine |
| | Spine Density | Low |
| | Tubercles (Warts) | No |
| | Flavor | Bitterfree |
| 6. | Fruit at Harvest Maturity | |
| | Length | 35-37 cm |
| | Diameter at Medial | 50-60 mm |
| | Color | Yellow |
| | Color Pattern | Striped |
| | Surface | Smooth |
| | Netting | Slight |
| | Fruit Set | Normally without seeds |
| 7. | Seeds | |
| | No. per Fruit | 30-80 |
| | Per 1,000 Seeds | 30-35 gm |
| 8. | Disease Resistance | |
| | Downy Mildew | Resistant |
| | Powdery Mildew (*Erysiphe cichoracearum*) | Resistant |
| | Cucumber Mosaic Virus | Susceptible |
| | Cucumber Vein Yellowing Virus | Susceptible |
| | Cucumber yellow Stunted Disorder Virus | Intermediate resistance |
| 9. | Insect Resistance | |
| | Aphid (*Aphis gossypii*) | Susceptible |

TABLE 4

Physiological and Morphological Characteristics of Line GSP 33-1094 GY.

| | CHARACTERISTIC | GSP 33-1094 GY |
|---|---|---|
| 1. | Type | Cucumber |
| | Predominate Usage | Pickling |
| | Predominate Culture | Outdoor |
| | Area of Best Adaptation in USA | Most Areas |
| 2. | Maturity | |
| | Days from Seeding to Market | 60-62 |
| 3. | Plant | |
| | Habit | Vine |
| | Growth | Indeterminate |
| | Sex | 100% Gynoecious |
| | Flower Color | Yellow |
| 4. | Stem | |
| | Length | 150-200 cm |
| | Number of Nodes from Cotyledon Leaves to Node Bearing the First Pistillate Flower | 3-4 |
| | Internode Length | 20-30 |
| | Stem Form | Grooved-Ridged |
| 5. | Leaf | Mature Blade of Third Leaf |
| | Length | 200-250 mm |
| | Width | 150-200 mm |
| | Petiole Length | 6.5-8 |
| 6. | Fruit at Edible Maturity | |
| | Length | 12-14 cm |
| | Diameter at Medial | 35-45 |
| | Weight | 80-120 gm |
| | Skin Color | Mottled or Speckled with yellow |
| | Yellowish Blossom End Strips | Extend Less than ⅓ of the Fruit Length |
| | Predominant Color at Stem End | Medium Green |
| | Predominant Color at Blossom End | Light Green (Arlington White Spine) |
| | Fruit Neck Shape | Not Necked |
| | Fruit Tapering | Ends Blunt or Rounded |
| | Stem End Cross Section | Square |

TABLE 4-continued

Physiological and Morphological Characteristics of Line GSP 33-1094 GY.

| CHARACTERISTIC | GSP 33-1094 GY |
|---|---|
| Medial Cross Section | Square |
| Blossom End Cross Section | Square |
| Skin Thickness | Thick |
| Skin Ribs | Ribbed |
| Skin Toughness | Tender |
| Skin Luster | Dull |
| Spine Color | White |
| Spine Quality | Fine |
| Spine Density | Many |
| Tubercles (Warts) | Few, Prominent (Salad) |
| Flavor | Bitterfree |
| 7. Fruit at Harvest Maturity | |
| Length | 25-30 cm |
| Diameter at Medial | 10-13 |
| Color | Cream |
| Color Pattern | Not Striped |
| Surface | Smooth |
| Netting | Slight or None |
| Fruit Set | Parthenocarpically |
| 8. Seeds | |
| No. per Fruit | 150-200 |
| Per 1,000 Seeds | 22-25 gm |
| 9. Disease Resistance | |
| Cucumber Scab (Gumosis) (*Cladosporium cucumerinum*) | Susceptible |
| Downy Mildew | Resistant |
| Powdery Mildew (*Erysiphe cichoracearum*) | Resistant |
| Target Spot (*Corynespora cassiicola*) | Susceptible |
| Cucumber Mosaic Virus | Resistant |
| 10. Insect Resistance | |
| Aphid (*Aphis gossypii*) | Susceptible |

TABLE 5

Physiological and Morphological Characteristics of Line GPN 33-1093 GY.

| CHARACTERISTIC | GPN 33-1093 GY |
|---|---|
| 1. Type | Cucumber |
| Predominate Usage | Pickling |
| Predominate Culture | Outdoor |
| Area of Best Adaptation in USA | Most Areas |
| 2. Maturity | |
| Days from Seeding to Market | 60-65 |
| 3. Plant | |
| Habit | Vine |
| Growth | Indeterminate |
| Sex | Primarily Gynoecious |
| Flower Color | Yellow |
| 4. Stem | |
| Length | 150-200 cm |
| Number of Nodes from Cotyledon Leaves to Node Bearing the First Pistillate Flower | 2-3 |
| Internode Length | 20-25 |
| Stem Form | Grooved-Ridged |
| 5. Leaf | Mature Blade of Third Leaf |
| Length | 200-230 mm |
| Width | 150-200 mm |
| Petiole Length | 4-8 |
| 6. Fruit at Edible Maturity | |
| Length | 11-13 cm |
| Diameter at Medial | 35-45 |
| Weight | 80-120 gm |
| Skin Color | Mottled or Speckled with yellow |
| Yellowish Blossom | Extend Less than |
| End Strips | ⅓ of the Fruit Length |
| Predominant Color at Stem End | Medium Green |
| Predominant Color at Blossom End | Light Green (Arlington White Spine) |
| Fruit Neck Shape | Not Necked |
| Fruit Tapering | Ends Blunt or Rounded |
| Stem End Cross Section | Square |
| Medial Cross Section | Square |
| Blossom End Cross Section | Square |
| Skin Thickness | Thick |
| Skin Ribs | Ribbed |
| Skin Toughness | Tender |
| Skin Luster | Dull |
| Spine Color | White |
| Spine Quality | Fine |
| Spine Density | Few |
| Tubercles (Warts) | Few, Prominent (Salad) |
| Flavor | Bitterfree |
| 7. Fruit at Harvest Maturity | |
| Length | 25-30 cm |
| Diameter at Medial | 10-13 |
| Color | Cream |
| Color Pattern | Striped |
| Surface | Smooth |
| Netting | Slight or None |
| Fruit Set | Normally with Seeds |
| 8. Seeds | |
| No. per Fruit | 150-200 |
| Per 1,000 Seeds | 22-25 gm |
| 9. Disease Resistance | |
| Cucumber Scab (Gumosis) (*Cladosporium cucumerinum*) | Susceptible |
| Downy Mildew | Resistant |
| Powdery Mildew (*Erysiphe cichoracearum*) | Resistant |
| Target Spot (*Corynespora cassiicola*) | Susceptible |
| Cucumber Mosaic Virus | Resistant |
| 10. Insect Resistance | |
| Aphid (*Aphis gossypii*) | Susceptible |

TABLE 6

Physiological and Morphological Characteristics: Line 03/8020-20_TUP03_DMFL_1.

| CHARACTERISTIC | 03/8020-20_TUP03_DMFL_1 |
|---|---|
| 1. Type | Cucumber |
| Predominate Usage | Fresh |
| Predominate Culture | Outdoor |
| Area of Best Adaptation in USA | Turkey & ½ East |
| 2. Maturity | |
| Days from Seeding to Market | 60-65 |
| 3. Plant | |
| Habit | Vine |
| Growth | Indeterminate |
| Sex | Monoecious |
| Flower Color | Yellow |
| 4. Stem | |
| Length | 150-200 cm |
| Internode Length | 30-50 mm |
| Stem Form | Grooved-Ridged |
| 5. Fruit at Edible Maturity | |
| Length | 12-15 cm |
| Diameter at Medial | 35-45 |
| Weight | 80-120 gm |
| Skin Color | Green |
| Yellowish Blossom End Strips | No |
| Predominant Color at Stem End | Uniform green |
| Predominant Color at Blossom End | Uniform green |

TABLE 6-continued

Physiological and Morphological Characteristics:
Line 03/8020-20_TUP03_DMFL_1.

| CHARACTERISTIC | 03/8020-20_TUP03_DMFL_1 |
|---|---|
| Fruit Neck Shape | Not Necked |
| Fruit Tapering | Ends Blunt or Rounded |
| Stem End Cross Section | rd |
| Medial Cross Section | rd |
| Blossom End Cross Section | rd |
| Skin Thickness | Thin |
| Skin Ribs | Not ribbed |
| Skin Toughness | Low |
| Skin Luster | Shiny |
| Spine Color | White |
| Spine Quality | Fine |
| Spine Density | High |
| Tubercles (Warts) | No |
| Flavor | Bitterfree |
| 6. Fruit at Harvest Maturity | |
| Length | 18-20 cm |
| Diameter at Medial | 30-45 mm |
| Color | Cream |
| Color Pattern | Striped |
| Surface | Smooth |
| Netting | Slight or None |
| Fruit Set | Normally with Seeds |
| 7. Seeds | |
| No. per Fruit | 150-200 |
| Per 1,000 Seeds | 22-25 gm |
| 8. Disease Resistance | |
| Cucumber Scab (Gumosis) (*Cladosporium cucumerinum*) | Resistant |
| Downy Mildew | Resistant |
| Powdery Mildew (*Erysiphe cichoracearum*) | Susceptible |
| Cucumber Mosaic Virus | Susceptible |
| 9. Insect Resistance | |
| Aphid (*Aphis gossypii*) | Susceptible |

TABLE 7

Physiological and Morphological Characteristics:
Line 03/8024-19_TUP03_DMFL_1.

| CHARACTERISTIC | 03/8024-19_TUP03_DMFL_1 |
|---|---|
| 1. Type | Cucumber |
| Predominate Usage | Fresh |
| Predominate Culture | Outdoor |
| Area of Best Adaptation in USA | Turkey & ½ East |
| 2. Maturity | |
| Days from Seeding to Market | 60-65 |
| 3. Plant | |
| Habit | Vine |
| Growth | Indeterminate |
| Sex | Monoecious |
| Flower Color | Yellow |
| 4. Stem | |
| Length | 150-200 cm |
| Internode Length | 30-50 mm |
| Stem Form | Grooved-Ridged |
| 5. Fruit at Edible Maturity | |
| Length | 15-17 cm |
| Diameter at Medial | 35-45 |
| Weight | 80-120 gm |
| Skin Color | Green |
| Yellowish Blossom End Strips | No |
| Predominant Color at Stem End | Uniform green |
| Predominant Color at Blossom End | Uniform green |
| Fruit Neck Shape | Not necked |
| Fruit Tapering | Ends blunt or rounded |
| Stem End Cross Section | rd |
| Medial Cross Section | rd |
| Blossom End Cross Section | rd |
| Skin Thickness | Thin |
| Skin Ribs | Not ribbed |

TABLE 7-continued

Physiological and Morphological Characteristics:
Line 03/8024-19_TUP03_DMFL_1.

| CHARACTERISTIC | 03/8024-19_TUP03_DMFL_1 |
|---|---|
| Skin Toughness | Low |
| Skin Luster | Shiny |
| Spine Color | White |
| Spine Quality | Fine |
| Spine Density | Low |
| Tubercles (Warts) | No |
| 6. Fruit at Harvest Maturity | |
| Length | 12-23 cm |
| Diameter at Medial | 30-45 mm |
| Color | Cream |
| Color Pattern | Striped |
| Surface | Smooth |
| Netting | Slight or none |
| Fruit Set | Normally with seeds |
| 7. Seeds | |
| No. per Fruit | 150-200 |
| Per 1,000 Seeds | 22-25 gm |
| 8. Disease Resistance | |
| Cucumber Scab (Gumosis) (*Cladosporium cucumerinum*) | Susceptible |
| Downy Mildew | Resistant |
| Powdery Mildew (*Erysiphe cichoracearum*) | Intermediate resistance |
| Cucumber Mosaic Virus | Resistant |
| 9. Insect Resistance | |
| Aphid (*Aphis gossypii*) | Susceptible |

TABLE 8

Physiological and Morphological Characteristics:
Line 03/8039-5_TUP03_DMFL_1.

| CHARACTERISTIC | 03/8039-5_TUP03_DMFL_1 |
|---|---|
| 1. Type | Cucumber |
| Predominate Usage | Fresh |
| Predominate Culture | Outdoor |
| Area of Best Adaptation in USA | Turkey & ½ East |
| 2. Maturity | |
| Days from Seeding to Market | 60-65 |
| 3. Plant | |
| Habit | Vine |
| Growth | Indeterminate |
| Sex | Monoecious |
| Flower Color | Yellow |
| 4. Stem | |
| Length | 150-200 cm |
| Internode Length | 30-50 mm |
| Stem Form | Grooved-Ridged |
| 5. Fruit at Edible Maturity | |
| Length | 16-18 cm |
| Diameter at Medial | 35-45 |
| Weight | 80-120 gm |
| Skin Color | Green |
| Yellowish Blossom End Strips | No |
| Predominant Color at Stem End | Uniform green |
| Predominant Color at Blossom End | Uniform green |
| Fruit Neck Shape | Not necked |
| Fruit Tapering | Ends blunt or rounded |
| Stem End Cross Section | rd |
| Medial Cross Section | rd |
| Blossom End Cross Section | rd |
| Skin Thickness | Thin |
| Skin Ribs | Not ribbed |
| Skin Toughness | Low |
| Skin Luster | Shiny |
| Spine Color | White |
| Spine Quality | Fine |
| Spine Density | Medium |
| Tubercles (Warts) | No |
| Flavor | Bitterfree |

TABLE 8-continued

Physiological and Morphological Characteristics:
Line 03/8039-5_TUP03_DMFL_1.

| CHARACTERISTIC | 03/8039-5_TUP03_DMFL_1 |
|---|---|
| 6. Fruit at Harvest Maturity | |
| Length | 20-24 cm |
| Diameter at Medial | 30-45 mm |
| Color | Cream |
| Color Pattern | Striped |
| Surface | Smooth |
| Netting | Slight or None |
| Fruit Set | Normally with Seeds |
| 7. Seeds | |
| No. per Fruit | 150-200 |
| Per 1,000 Seeds | 22-25 gm |
| 8. Disease Resistance | |
| Cucumber Scab (Gumosis) (*Cladosporium cucumerinum*) | Resistant |
| Downy Mildew | Resistant |
| Powdery Mildew (*Erysiphe cichoracearum*) | Intermediate resistance |
| Cucumber Mosaic Virus | Susceptible |
| 9. Insect Resistance | |
| Aphid (*Aphis gossypii*) | Susceptible |

In one embodiment, the invention provides a DM resistant cucumber plant, or the fruit or seeds thereof, wherein the cucumber plant demonstrates a reduction in foliar symptoms of chlorotic and/or necrotic lesions relative to a non-resistant control plant upon inoculation or infection with DM, and wherein said plant demonstrates resistance to one or more of *Verticillium* wilt, root knot nematodes, tobacco mosaic virus, cucumber scab, powdery mildew, target spot, cucumber mosaic virus, *papaya* ringspot virus, zucchini yellow mosaic virus, and *Fusarium* wilt. In another embodiment, those cucumber plants, or the fruit or seeds thereof, are selected from DM resistant progeny of lines described in Tables 1-8. In other embodiments, a DM resistant cucumber plant that also demonstrates resistance to one or more of: *Verticillium* wilt, cucumber scab, powdery mildew, target spot, cucumber mosaic virus, nematodes, tobacco mosaic virus *papaya* ringspot virus, zucchini yellow mosaic virus, and *Fusarium* wilt displays a greater than 10% reduction, or a greater than 30% reduction, or a greater than 60% reduction in foliar symptoms of chlorotic and/or necrotic lesions upon inoculation or infection with DM. In some aspects, the cucumber plants are adapted either for greenhouse growth or for field growth.

One aspect of the invention provides a DM cucumber plant, or the fruit or seeds thereof, wherein the cucumber plant, or the fruit thereof, expresses one, or two, or three, or more independently selected desirable traits in addition to DM resistance. In one embodiment, the "desirable trait" or "desirable traits" are selected from the group consisting of: fruit size, shape, color, surface appearance; seed number, seed size, locule number; pericarp thickness and toughness; taste, bitterness, the presence of tubercles, and shelf life, plant vigor, leaf shape, leaf length, leaf color, plant height, whether the plant is determinate or not, time to maturity, adaptation to field growth, adaptation to greenhouse growth, and resistance to one or more diseases or disease causing organisms such as *Verticillium* Wilt, root knot nematodes, Tobacco Mosaic Virus, Cucumber Scab, Powdery Mildew, Downy Mildew, Target Spot, Cucumber Mosaic Virus, and *Fusarium* Wilt. In another embodiment the "desirable trait" or "desirable traits" are selected from the group consisting of: fruit size, fruit shape, fruit color, fruit taste, the number of seeds per fruit, the size of seeds, the thickness of fruit pericarp tissue, the shelf life of fruit, resistance to *Verticillium* Wilt, resistance to Cucumber Scab, resistance to Powdery Mildew, resistance to Target Spot, resistance to Cucumber Mosaic Virus, resistance to nematodes, resistance to Tobacco Mosaic Virus, resistance to *Papaya* Ringspot Virus, resistance to Zucchini Yellow Mosaic virus, and resistance to *Fusarium* Wilt. In yet another embodiment, the "desirable trait" or "desirable traits" are selected from the group consisting of: fruit size, fruit shape, fruit color, fruit taste, the shelf life of fruit, resistance to Cucumber scab, resistance to Powdery mildew, resistance to Target spot, and resistance to Cucumber mosaic Virus. In still another embodiment the "desirable trait" or "desirable traits" are selected from the group consisting of: fruit size, fruit shape, fruit color, fruit quality acceptable to market, and the shelf life of fruit.

In other aspects of the invention, the plants bearing one or more desirable traits in addition to DM resistance display a greater than 10%, or a greater than 30%, or a greater than 60%, or a greater than 80% reduction in foliar symptoms of chlorotic and/or necrotic lesions relative to a non-resistant control plant upon inoculation or infection with DM. Another aspect of the present invention is directed to a method of producing a DM resistant cucumber plant comprising: crossing a cucumber line having DM resistance with a second plant lacking DM resistance but capable of donating one or more of the aforementioned desirable traits.

EXAMPLES

Example 1: Downy Mildew Culture and Disease Screening—Field

*Pseudoperonospora cubensis* (Berk. et Curt.) Rostow is an obligate pathogen. Therefore, it must be maintained on live plants of a susceptible cucurbit. Two isolates were used in screening for resistance in this study. The "old" isolate of *P. cubensis* is characterized by its pathogenicity on both squash and cucumber. The "new" isolate of *P. cubensis* is not considered pathogenic on squash but is very pathogenic on cucumber. The pathogen was stored by freezing leaves or cotyledons with abundant sporulation at −80° C. Although there may be some loss in spore viability inherent in the freezing process, no decrease in viability over time once spores are frozen, has been found. Six weeks before spreader host plants were to be transplanted in the field, susceptible cucumber hosts were planted in a controlled environment chamber. At three weeks they were inoculated with a spore suspension derived from infected leaves stored in a −80° C. freezer. Inoculated culture plants were maintained at 20° C.; once chlorotic lesions have developed, plants were placed in the dew chamber overnight to induce sporulation. This culture was transferred weekly on cucumber until plants were transplanted into the field.

Trials were direct seeded in the field. Spreader rows of susceptible cucumber were planted in every third row. When spreader rows were two-three weeks old, infected plants (reared in the growth room) were transplanted within the spreader rows. Breeder trials were done simultaneously. Plots were maintained in good horticultural condition, consistent with techniques normally employed for culture of cucumbers in the Southeast.

Spreader plants at the three to four leaf stage were inoculated in the greenhouse by misting with sporangial suspension using a spray bottle. Inoculum was formulated in sterile distilled water. After inoculation, plants were placed in dew chamber at 100% RH and 20° C., for 18-24 hours. Spreader plants were transplanted to the field where a solid set sprinkler provided a nightly moist period to encourage development and spread of disease.

Tests were evaluated once symptoms had developed on the susceptible check, sometimes called the susceptible control. Controls including PI197088 (resistant control); DMP21, GP14, LLP 1, POINSETT 76, (intermediate-resistant controls); and SPRINT440, MARAM, and SMR58 (susceptible controls) were used. Three observations were made on each plot, one at each end and one in the middle. The mean disease index for each plot was calculated. These were averaged for all three replicates and the standard deviation was determined. The disease index ranges for the categories "Resistant," "Intermediate Resistant" and "Susceptible" were then determined. Varieties were generally trialed several times before a final disease resistance level determination was made. A completely randomized design was used in the disease test. Each line was replicated three times—approximately 40 plants per entry were tested. Lines with limited seed available were included as a single rep observation plot. Checks were included as entries to gauge the severity of the test. Plots were 12 feet long with a 3-foot alley between ends of blocks. A susceptible spreader was planted in every third row and on the outside borders of the entire planting Example 2: Downy Mildew Culture and Disease Screening—Greenhouse

*Pseudoperonospora cubensis* (Berk. et Curt.) Rostow, as described and stored above in Example 1, was also used for greenhouse screens. Two weeks prior to screen inoculation, susceptible cucumber hosts were sown in seedling trays. At one week post planting, the seedlings are inoculated with a rate of approximately $5 \times 10^4$ sporangia/mi. The inoculated hosts were then placed into a growth chamber and maintained for seven days at about 70° F. After seven days, the seedlings were placed into a dew chamber overnight to induce sporulation. This culture was transferred onto susceptible cucumber hosts on a weekly basis.

Cotyledon screens were planted in seedling trays. Susceptible and resistant checks were planted on both sides of each tray. Plants were seeded and maintained in a greenhouse at 80° F. Inoculation was conducted at 7 to 10 days for cotyledons and at the 5th leaf stage for true leaves. Plants were inoculated by misting with sporangial suspension using a spray bottle at a concentration of about $5 \times 10^4$ sporangia per ml for cotyledons and $1 \times 10^4$ to $3 \times 10^4$ for true leaves. After inoculation, plants were placed in a dew chamber at 100% relative humidity and 20° C., for 18-24 hours.

Tests were evaluated once symptoms have developed on the susceptible check, sometimes called the susceptible control. Controls used were PI197088 (resistant control) MARAM (susceptible control), and SMR58 (resistant control). Resistant and intermediate survivors of the cotyledon screens were kept and transplanted into 3-inch peat pots to be inoculated again or to be transplanted into greenhouse grow bags. Resistant and intermediate survivors of the true leaf screens were transplanted directly into greenhouse grow bags.

Example 3: Introgression of DM Resistance into Cucumber Lines

Downy Mildew resistance identified in the Plant Introduction line PI197088 was found to be stable in multiple screening locations worldwide and against both older (pathogenic on squash and cucumber) and newly emerged (not considered pathogenic on squash and very pathogenic on cucumber) isolates of *P. cubensis*. However, both plants and fruit of PI197088 are commercially unacceptable. A locus contributing to Downy Mildew resistance in PI197088 was mapped with molecular markers as described in Example 4. A total of about 128 cucumber lines were separately screened using one or both DM isolates. DNA is isolated from resistant lines to screen for marker polymorphisms between the donor and recurrent parents.

Included in these screens are cucumber varieties Conquistador, Crispina, DMP21, and PI197088, among others, which are resistant of intermediate-resistant. Also included are Colt, Sprint440, Talladega, Lucinde, and Serena, among others, as susceptible control lines. Tissue samples from each of the DM resistant lines were collected for use in DNA analysis and production of a DNA library to identify markers associated with DM resistance. Seeds were also obtained from each of the lines demonstrating DM resistance generally via mixed pollen pollinations within each accession, and where possible via selfing. Mixed pollen pollinations were generally used in wild type cucumbers as they often contain a self-incompatibility factor.

Initial crosses were made between PI197088 and a recurrent susceptible parent to create $F_1$ plants. Plants derived from these crosses were used for disease testing as described in Examples 1 and/or 2. Experiments were performed to screen for DM resistance on a collection of elite lines that show horticulturally acceptable plant and fruit types, and should have the DM resistance introgressed from PI197088. These tests were performed in three locations (Woodland, Calif., Tifton, Ga., and Wageningen, NL) and used two isolates of *Pseudoperonospora cubensis*: an "older" isolate, pathogenic on squash and cucumber, and the putative "new" isolate, not considered pathogenic on squash but very virulent on cucumber. Simultaneously, these samples were genotyped with molecular markers to identify a QTL contributing DM resistance in PI197088 (see also Example 4). These tests associate the DM pathology response with the presence of an allele from PI197088. During this time, breeders submitting the samples assembled all trial data available on these lines in which plant and fruit types are noted or quantified. The following lines shown in Tables 9-10 were screened for resistance to Downy Mildew.

TABLE 9

Pedigrees for Cucumber Lines for which a Seed Deposit was Made.
Isolate of DM

| Cucumber Line | Pedigree |
|---|---|
| ASL147-2027 | PI-197088-MO/ASL-1105-GY:@.1.1.1.1.4. |
| EUR154-1012GY | [(ALCOR(WMV)xVENTURAxPIDM/NIZ335*2)X(ALCOR(V)xVENTURAxPIDM/CARMEN*2)]X[(ALCOR(V)xVENTURAxPIDM/CARMEN*2)X(ALCOR(V)xVENTURAxPIDM/CARMEN*2)] |
| EUR154-1021GY | (ALCOR(WMV)xVENTURAxPIDM/NIZ335*2)X(ALCOR(V)xVENTURAxPIDM/CARMEN*2) |
| GSP33-1094GY | F9-(Jazz/5/Sal//SMR-58Nim/PiHoNi/3/NO-50/4/H-171wit/SMR-58Nim//Carol/3/NO-50 * Harmonie) |
| GPN33-1093GY | F8-(Jazz/5/Sal//SMR-58Nim/PiHoNi/3/NO-50/4/H-171wit/SMR-58Nim//Carol/3/NO-50) |
| 03/8020-20_TUP03_DMFL_1 | BA.KO {(147W*PI)*225)} * (BA MO*part) BC4 03/8020-20_TUP03_DMFL_1+---1_TUNE03_DM-2_TUp05_TKFA06 |
| 03/8024-19_TUP03_DMFL_1 | BA.KO {(147W*PI)*225)} * [(me/n*147wmv)bc4f5*(bamo*parth)bc4f5] 03/8024-19_TUP03_DMFL_1+---4_TUNE03_DM-1_TUp05_TKFA06 |
| 03/8039-5_TUP03_DMFL_1 | BA.KO {(147W*PI)*225)} * HP 159] * [(BA MO*part) BC4 03/8039-5_TUP03_DMFL_1+---3_TUNE03_DM-4_TUp05_TKFA06 |

TABLE 10

Marker haplotypes and associated Downy Mildew (DM) reaction
scores for five markers in the DM resistance QTL region.
Data represent thirty seven cucumber lines.

| Marker | cM[1] position | Hap[2]. 1 | Hap. 2 | Hap. 3 | Hap. 4 | Hap. 5 |
|---|---|---|---|---|---|---|
| Markers and sample haplotypes | | | | | | |
| CAPs_ENK60 | 4 | SUS[3] | SUS | RES[4] | RES | RES |
| CAPs_ENK59 | 5 | SUS | SUS | RES | RES | RES |
| CAPs_17170 | 11 | SUS | SUS | SUS | SUS | RES |
| CAPs_17179 | 11 | SUS | SUS | SUS | SUS | RES |
| CAPs_17563/66 | 39 | SUS | RES | SUS | RES | RES |
| Downy Mildew summary statistics associated with marker haplotypes | | | | | | |
| Mean (DM[5]) | | 4.8 | 4.5 | 4.0 | 2.2 | 3.3 |
| Minimum (DM) | | 4.3 | 3.3 | 3.7 | 1.0 | 1.0 |
| Maximum (DM) | | 5.0 | 5.0 | 4.3 | 3.3 | 5.0 |
| Std. Deviation (DM) | | 0.2 | 0.6 | 0.3 | 0.5 | 1.2 |
| Number of lines with haplotype | | 3 | 3 | 1 | 19 | 11 |

[1]cM = centiMorgans.
[2]Hap = Haplotype at five markers in DM QTL.
[3]SUS = Downy Mildew susceptible allele associated with Lucinde parent in mapping population.
[4]RES = Downy Mildew resistance allele associated with PI197088 parent in mapping population.
[5]DM = phenotypic scores in a pathology test for Downy Mildew.

Thirty seven cucumber lines were tested for reactions to *Pseudoperonospora cubensis* in a controlled pathology screen. Eighteen plants were tested in three replicates of six plants. From each replication, three plants (total from three replications=9) were genotyped for five markers defining the DM QTL region. From these data, consensus marker genotypes and DM summary statistics were developed for each line. These data are summarized in Table 10. The five markers used in this test were selected from the eight linked markers in the DM QTL. The five markers were selected based on reliable performance in the laboratory, and for associations with DM phenotype that were more consistent than the other markers.

Table 10 supports association of the haplotype RES-RES-SUS-SUS-RES at the markers CAPs_ENK60, CAPs_ENK59, CAPs_17170, CAPs_17179, CAPs_17563/66 with a more DM resistant phenotype. Substitution of the SUS allele with the RES allele at markers CAPs_ENK60, CAPs_ENK59, CAPs_17563/66 yields a change in mean DM phenotype from 4.8 to 2.2 in tests where 1=resistant and 5=susceptible.

Example 4: Marker Analysis of DM Resistant Cucumber Plants

Figure 2:
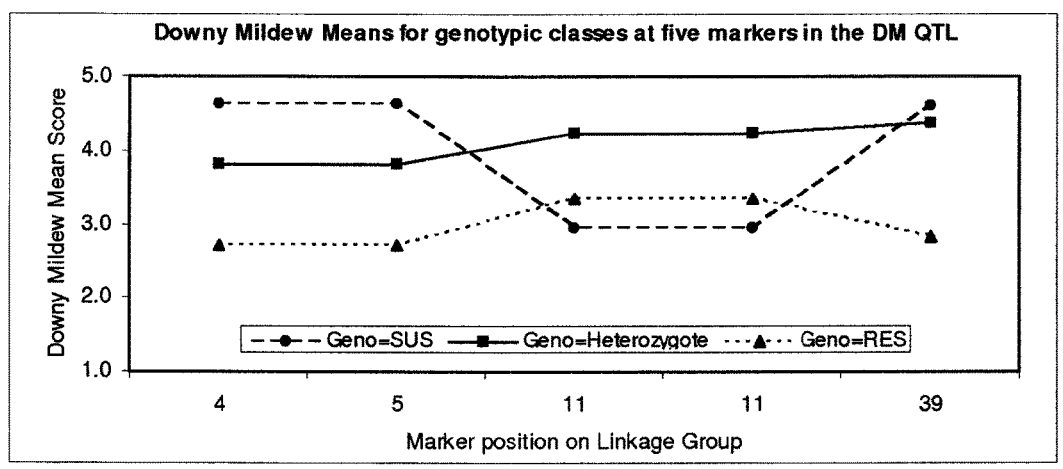
FIG. 2 depicts Downy Mildew resistance data for certain additional markers in an identified Downy Mildew resistance contributing QTL region, showing correlation between DM resistance and marker position.

Resistant plants are analyzed using genetic markers distributed throughout the cucumber genome. Genetic markers for *Cucumis* are available from a variety of sources such as USDA-ARS (Vegetable Crops Research Unit—Department of Horticulture, University of Wisconsin-Madison). A larger set of markers was pre-screened on the parental lines and polymorphic markers were selected, from among the pre-screened markers, for a subsequent screen. A correlation was then established with most of the resistant plants and the presence of specific donor alleles, for instance as shown in Table 10 and FIG. 2. Most of the resistant plants contained introgressed DNA from the resistant donor line, PI19788, for instance at loci as shown in FIG. 2. A multiple regression model was constructed to retain the markers that contributed to the DM resistance phenotype. In this analysis, markers CAPs_ENK60, CAPs_17170, and CAPs_17563/66 remained significant, generating a model with $R^2$ of 0.47.

Primer pairs and reaction conditions utilized to define the QTL for DM resistance in *Cucumis* sp. are shown in Table 11 and Table 12.

TABLE 11

Primer pairs used (SEQ ID Nos: 1 to 17).

| Marker name | Forward Primer (5' to 3') | Reverse Primer (5' to 3') | Enzyme | Electro-phoresis condition | Notes |
|---|---|---|---|---|---|
| CAPs_21826 | TCAAGCCATAGTCTAACCCATGC | CGCTATATCATGGATGGCTAGAAAT | NsiI | 3% agarose gel | |
| CAPs_ENK60 | GAATAGATAGGCTACACTTTTCCCTCTTG | GTATAAAACTTGAGTGAATTTAATGCATGAA | HpyC H4 IV | 3% agarose gel | |
| CAPS_ENK59 | TGTTTCATAACTACAGCTTCATGTTAAATATTACT | TAGTTTCTTTCTTGCTGGACGAACC | | 3% agarose gel | |
| CAPs_17170 | TATGGGCTATGTGAAACTCTT | AGCGTGACAACTACAAAACAT | Afl III | 3% agarose tel | |
| CAPs_17179 | GAAATAAATGGATGAAGCGAGGA | GTTCGTTGATCAGTGTGATATTTCAAT | | Capillary | Forward primer for P1197088 allele |
| CAPs_17179 | ATCGGTCTTTGCCACCTTTTG | GTTCGTTGATCAGTGTGATATTTCAAT | | Capillary | Forward primer for Lucinde allele |
| CAPs_18229 | TGTTTGGAAGGGTTTCTTGGG | TGCCATGTCGCCAACAGT | HindIII | 3% agarose gel | |
| CAPs_17563/66 | AGGAGGGACAGAGAGAATTTGATATAAT | CGTTTTAGGTGATTGTCATCAATACAT | | Capillary | |
| CAPs_ENK70 | AAAGTTGATAGTGCATGAGTTGGTAAAATA | TCCGCTTATGGGTTTTTGTGAG | Taq1 | 3% agarose gel | |

TABLE 12

Reaction conditions for PCR.

| Component | Combine per 10 ul rxn | Master Mix for 10: |
|---|---|---|
| PCR for: Markers run on agarose gel (CAPs_ENK60, CAPs_ENK59, CAPs_17170, CAPs_18229, CAPs_21826, CAPs_ENK70) | | |
| HotStart-IT Taq Master Mix (2X) | 5 | 50 |
| 5 uM Forward Primer | 0.53 | 5.3 |
| 5 uM Reverse Primer | 0.53 | 5.3 |
| MQ H₂O | 3.14 | 31.4 |
| Template DNA | 0.8 | 8 |
| Sum | 10 | 100 |
| PCR for: CAPs_17179 | | |
| HotStart-IT Taq Master Mix (2X) | 5 | 50 |
| 5 uM Primer 1 | 0.53 | 5.3 |
| 5 uM Primer 2 | 0.53 | 5.3 |
| 5 uM Tailed Primer | 0.053 | 0.53 |
| Labeled primer 1475 | 0.53 | 5.3 |
| MQ H₂O | 2.557 | 25.57 |
| Template DNA | 0.8 | 8 |
| Sum | 10 | 100 |
| PCR for: CAPs_17563/66 | | |
| HotStart-IT Taq Master Mix (2X) | 5 | 50 |
| 5 uM Primer | 0.53 | 5.3 |
| 5 uM Tailed Primer | 0.053 | 0.53 |
| Labeled primer 1475 | 0.53 | 5.3 |
| MQ H₂O | 3.087 | 30.87 |
| Template DNA | 0.8 | 8 |
| Sum | 10 | 100 |

Analysis for the genetic markers was performed by PCR amplification. PCR reactions were conducted as follows: PCR reactions contain 1.0 microliters of cucumber genomic DNA (10 ng), 2 µl 10×PCR Buffer (ABI PCR Buffer I: part no. N808-0006), 1.0 µl 10×dNTP mix (final concentration of each dNTP is 250 µM), 1 µl each primer (5 picomoles of each primer), 0.2 µl Taq Polymerase (1 unit), and sterile water to a total volume of 20 microliters. PCR reactions are incubated for 2 minutes at 94° C., 30 seconds at 94° C., 30 seconds at 50° C., and 90 seconds at 72° C. for 35 cycles, followed by a single cycle of 72° C. for 5 minutes. PCR reactions are performed for instance on an ABI9700 PCR machine (Applied Biosystems, Foster City, Calif.).

Sequencing of genomic DNA flanking the loci initially screened in the QTL region could explain some of the variability that was seen in some DM resistance scores. For instance, in certain lines with resistant haplotypes, but variable resistance scores, variability could be seen near the CAPs_17170 marker. Thus, when sequences for alleles at this locus were compared between two given lines with differing DM resistance scores, they may have matched at the position exploited for the marker assay, and so both could be defined as the same genotype. However, the sequences of such lines were found in some cases to differ for instance by up to 3 SNPs at sites near to but not exploited by the marker assay.

Plants containing a DM resistant donor allele(s), including lines GSP33-1094GY and GPN33-1093, among others (see Tables 1-8, and 13) were selected for further breeding. Depending on the breeding strategy, plants selected for further breeding can be either homozygous or heterozygous for a donor (resistant) allele.

TABLE 13

Line Descriptions- Selected Agronomic and Disease Resistance Traits for Additional Lines with Introgressed DM Resistance and Comparison Lines.

| Line Code | Seed Source | Type | Flowering pattern | Parthenocarpic | Plant-bitterfree | CMV | Scab (*Cladosp. Cuc.*) | PM (*Sphaerotheca f.*) | DM (*Pseudop. Cu.*) | Smooth/ Spined | Spine color |
|---|---|---|---|---|---|---|---|---|---|---|---|
| Lines with a high level of DM-resistance | | | | | | | | | | | |
| 05-346 | NJ05 854-3 | Pickling, parth. spined | GY | Yes | Yes | 1 | 1 | 2 | 2 | Spined | White |
| GSP33-1094GY | NJ05 696-4 | Pickling, parth. smooth | GY | Yes | No | 2.5 | 5 | 1 | 2 | Smooth | xxxxx |
| 01-349 | VJ02 322-6 | Pickling, parth. spined | GY | Yes | Yes | 1.5 | 1 | 1 | 2 | Spined | White |
| GPN33-1093GY | VJ02 55-3 | Pickling, poll. spined | GY | No | No | 3 | 5 | 2 | 2 | Spined | White |
| Lines susceptible to DM | | | | | | | | | | | |
| 05-110 | VJ05 110-3 | Pickling, parth. smooth | GY | Yes | Yes | 2 | 1 | 1 | 4 | Smooth | xxxxx |
| 01-714 | NJ05 684-4 | Pickling, parth. smooth | GY | Yes | Yes | 2 | 1 | 2 | 4 | Smooth | xxxxx |
| 05-779 | VJ05 273-4 | Riesenschal parth. | GY | Yes | Yes | 5 | 5 | 5 | 5 | Smooth | xxxxx |

| Line Code | Seed Source | Type | CAPs_ENK59 | CAPs_ENK60 | CAPs_17179 | CAPs_17170 | CAPs_18229 | CAPs_17563/66 | DM Mean score |
|---|---|---|---|---|---|---|---|---|---|
| Lines with a high level of DM-resistance | | | | | | | | | |
| 05-346 | NJ05 854-3 | Pickling, parth. spined | B | B | B | B | A | B | 1.8 |
| GSP33-1094GY | NJ05 696-4 | Pickling, parth. smooth | B | B | A | A | A | B | 2.0 |
| 01-349 | VJ02 322-6 | Pickling, parth. spined | B | B | B | B | A | B | 2.3 |
| GPN33-1093GY | VJ02 55-3 | Pickling, poll. spined | B | B | A | A | A | B | 1.8 |
| Lines susceptible to DM | | | | | | | | | |
| 05-110 | VJ05 110-3 | Pickling, parth. smooth | B | B | B | B | A | B | 3.6 |
| 01-714 | NJ05 684-4 | Pickling, parth. smooth | B | B | B | B | A | B | 4.1 |
| 05-779 | VJ05 273-4 | Riesenschal parth. | A | A | A | A | A | A | 5.0 |

Line 05-346 was found to display strong vigour, with dark green fruit color and cylindric fruits with a length/thickness ratio of 3.2. Line GSP33-1094GY was found to display strong vigour, with fruits rather long (length/thickness ratio of 3.3/3.4), and leaves somewhat upright with little leaf tendency. The skin of the fruit was somewhat rough. Line 01-349 was found to be productive, with good fruit shape. Fruit flesh was firm, and fruits displayed an average length/thickness ratio of 3.3. Line GPN33-1093GY displayed strong vigour. Leaves were somewhat curled. Its fruits were slightly spined, but the density of spines was very low. The average length/thickness ratio of fruits was 3.3.

Deposit Information

A deposit of 1000 seeds has been, or will be, made of the *Seminis* Vegetable Seeds proprietary lines ASL147-2027, EUR154-1012GY, EUR154-1021GY, GSP33-1094GY, and GPN33-1093GY, disclosed above and encompassed in the appended claims, with the American Type Culture Collection (ATCC), Manassas, Va. 20110-2209 USA, an International Depositary Authority (IDA) as established under the Budapest Treaty on the International Recognition of the Deposit of Micro-organisms for the Purposes of Patent Procedure. The accession numbers for lines ASL147-2027, EUR154-1012GY, EUR154-1021GY, GSP33-1094GY, and GPN33-1093GY are ATCC Accession No. PTA-9375, ATCC Accession No. PTA-8930, ATCC Accession No. PTA-8931, ATCC Accession No. PTA-8953, and ATCC Accession No. PTA-8954. The dates of deposit were Jul. 15, 2008, Feb. 11, 2008, Feb. 11, 2008, Feb. 20, 2008, and Feb. 20, 2008, respectively. Upon issuance of a patent, all restrictions upon the deposits will be removed, and the deposits are intended to meet all of the requirements of 37 C.F.R. §1.801-1.809.

What is claimed is:

1. An agronomically elite Downy Mildew resistant cucumber plant comprising the genetic source for said resistance to Downy Mildew found in accession PI197088, and wherein the presence of said genetic source is characterized by the presence of at least a first genetic marker selected from the group consisting of CAPs_21826, CAPs_ENK60, CAPs_ENK59, CAPs_17170, CAPs_17179, CAPs_18229, CAPs_17563/66, and CAPs_ENK70, wherein the plant is produced by a method comprising:
   (a) crossing a cucumber plant of accession PI197088 with a second cucumber plant having at least one desired trait; and
   (b) selecting at least a first progeny cucumber plant resulting from the crossing that comprises resistance to Downy Mildew and the desired trait.

2. The Downy Mildew resistant cucumber plant of claim 1, wherein the desired trait is selected from the group consisting of: fruit size, shape, color, surface appearance; seed number, seed size, locule number; pericarp thickness and toughness; taste, bitterness, the presence of tubercles, shelf life, plant vigor, leaf shape, leaf length, leaf color, plant height, whether the plant is determinate or not, time to maturity, adaptation to field growth, adaptation to greenhouse growth, fruit quality acceptable to market, and resistance to one or more diseases or disease causing organisms selected from the group consisting of *Verticillium* wilt, root knot nematodes, Tobacco Mosaic Virus, Cucumber scab, Powdery mildew, Target spot, Cucumber Mosaic Virus and *Fusarium* wilt, *Papaya* Ringspot Virus, and Zucchini Yellow Mosaic Virus.

3. The Downy Mildew resistant cucumber plant of claim 1, wherein selecting the first progeny comprises identifying the presence of at least a first genetic marker in the first progeny that is genetically linked to a locus contributing to Downy Mildew resistance.

4. The Downy Mildew resistant cucumber plant of claim 3, wherein selecting the first progeny further comprises selecting the progeny based on the presence of a plurality of genetic markers from the second cucumber plant present in the progeny.

5. The Downy Mildew resistant cucumber plant of claim 3, wherein the genetic marker is selected from the group consisting of markers CAPs_21826, CAPs_ENK60, CAPs_ENK59, CAPs_17170, CAPs_17179, CAPs_8229, CAPs_7563/66, and CAPs_ENK70.

6. The Downy Mildew resistant cucumber plant of claim 5, wherein the genetic marker is selected from the group consisting of CAPs_ENK60, CAPs_17170, and CAPs_17563/66.

7. The Downy Mildew resistant cucumber plant of claim 1, wherein the method further comprises the step of:
(c) crossing the progeny plant with itself or a third plant to produce a progeny plant of a subsequent generation.

8. The Downy Mildew resistant cucumber plant of claim 7, wherein the method further comprises the steps of:
(d) crossing the progeny plant of a subsequent generation with itself or a second plant; and
(e) repeating steps (c) and (d) for an additional 3-10 generations to produce an inbred cucumber plant derived from the cucumber accession PI197088.

9. The Downy Mildew resistant cucumber plant of claim 8, wherein said progeny plant of a subsequent generation is selected for crossing based on the presence of resistance to Downy Mildew and the desired trait.

10. The Downy Mildew resistant cucumber plant of claim 9, wherein the progeny plant of a subsequent generation is selected at each generation for crossing based on the presence of the resistance to Downy Mildew and the desired trait.

11. The Downy Mildew resistant cucumber plant of claim 9, wherein selecting the progeny plant of a subsequent generation comprises identifying the presence of at least a first genetic marker in the first progeny that is genetically linked to a locus contributing to Downy Mildew resistance.

12. The Downy Mildew resistant cucumber plant of claim 11, wherein selecting the progeny plant of a subsequent generation further comprises selecting the progeny based on the presence of a plurality of genetic markers from the second cucumber plant present in the progeny.

13. The Downy Mildew resistant cucumber plant of claim 8, wherein step (e) is repeated a sufficient number of generations to obtain an inbred cucumber plant that comprises the resistance to Downy Mildew and otherwise comprises the agronomic traits of the second cucumber plant.

14. A seed of the Downy Mildew resistant cucumber plant of claim 1.

15. A plant part of the Downy Mildew resistant cucumber plant of claim 1.

16. The plant part of claim 15, wherein said part is selected from the group consisting of a leaf, fruit, pollen, an ovule and a cell.

17. The Downy Mildew resistant cucumber plant of claim 1, wherein said cucumber plant comprises the genetic source for expressing Downy Mildew resistance from a line selected from the group consisting of ASL147-2027, a sample of the seed of which has been deposited under ATCC Accession Number PTA-9375; EUR154-1012GY, a sample of the seed of which has been deposited under ATCC Accession Number PTA-8930; EUR154-1021GY, a sample of the seed of which has been deposited under ATCC Accession Number PTA-8931; GSP33-1094GY, a sample of the seed of which has been deposited under ATCC Accession Number PTA-8953; and GPN33-1093GY, a sample of the seed of which has been deposited under ATCC Accession Number PTA-8954.

18. The Downy Mildew resistant cucumber plant of claim 17, wherein said cucumber plant is a plant of a line selected from the group consisting of ASL147-2027, a sample of the seed of which has been deposited under ATCC Accession Number PTA-9375; EUR154-1012GY, a sample of the seed of which has been deposited under ATCC Accession Number PTA-8930; EUR154-1021GY, a sample of the seed of which has been deposited under ATCC Accession Number PTA-8931; GSP33-1094GY, a sample of the seed of which has been deposited under ATCC Accession Number PTA-8953; and GPN33-1093GY, a sample of the seed of which has been deposited under ATCC Accession Number PTA-8954.

* * * * *